(12) United States Patent
Szalay et al.

(10) Patent No.: US 12,036,278 B2
(45) Date of Patent: *Jul. 16, 2024

(54) SMALLPOX VACCINE FOR CANCER TREATMENT

(71) Applicant: CALIDI BIOTHERAPEUTICS (NEVADA), INC., San Diego, CA (US)

(72) Inventors: Aladar Szalay, Highland, CA (US); Boris Minev, San Diego, CA (US)

(73) Assignee: Calidi Biotherapeutics (Nevada), Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/103,214

(22) Filed: Jan. 30, 2023

(65) Prior Publication Data

US 2023/0173062 A1   Jun. 8, 2023

Related U.S. Application Data

(63) Continuation of application No. 17/089,527, filed on Nov. 4, 2020, now Pat. No. 11,607,450, which is a continuation of application No. 16/044,136, filed on Jul. 24, 2018, now Pat. No. 10,857,225, which is a continuation of application No. 15/235,082, filed on Aug. 11, 2016, now Pat. No. 10,105,436.

(60) Provisional application No. 62/317,226, filed on Apr. 1, 2016, provisional application No. 62/216,292, filed on Sep. 9, 2015, provisional application No. 62/203,835, filed on Aug. 11, 2015.

(51) Int. Cl.
| | | |
|---|---|---|
| *A61K 39/285* | (2006.01) | |
| *A61K 35/35* | (2015.01) | |
| *A61K 35/76* | (2015.01) | |
| *A61K 39/12* | (2006.01) | |
| *A61K 39/00* | (2006.01) | |

(52) U.S. Cl.
CPC ............ *A61K 39/285* (2013.01); *A61K 35/35* (2013.01); *A61K 35/76* (2013.01); *A61K 39/12* (2013.01); *A61K 2039/515* (2013.01); *A61K 2039/525* (2013.01); *A61K 2039/5254* (2013.01); *A61K 2039/55* (2013.01); *A61K 2039/585* (2013.01); *A61K 2039/6006* (2013.01); *C12N 2710/24134* (2013.01)

(58) Field of Classification Search
CPC .......... C12N 2710/24134; A61P 35/00; A61P 35/02; A61K 2039/515; A61K 35/35; A61K 2039/585; A61K 49/00; A61K 2123/00; A61K 2121/00; A61K 2236/00; A61K 2039/80; A61K 39/275; A61K 2035/124; A61K 35/13; A61K 2039/525; A61K 2039/5254; A61K 39/12; A61K 39/285

See application file for complete search history.

(56) References Cited

U.S. PATENT DOCUMENTS

| | | | | |
|---|---|---|---|---|
| 7,588,771 | B2 | 9/2009 | Szalay et al. | 424/232.1 |
| 7,662,398 | B2 | 2/2010 | Szalay et al. | 424/232.1 |
| 7,754,221 | B2 | 7/2010 | Szalay et al. | 424/199.1 |
| 8,021,662 | B2 | 9/2011 | Szalay et al. | 424/138.1 |
| 8,221,769 | B2 | 7/2012 | Szalay et al. | 424/232.1 |
| 8,445,275 | B2 | 5/2013 | Hochrein et al. | 435/372 |
| 8,691,502 | B2 | 4/2014 | Kupper et al. | 435/5 |
| 8,859,256 | B2 | 10/2014 | Szalay et al. | 435/210 |
| 9,492,534 | B2 | 11/2016 | Szalay et al. | 424/199.1 |
| 10,105,436 | B2 * | 10/2018 | Szalay | A61K 35/76 |
| 10,238,699 | B2 | 3/2019 | Aboody et al. | 424/93.21 |
| 10,709,745 | B2 | 7/2020 | Aboody et al. | 424/93.21 |
| 10,857,225 | B2 * | 12/2020 | Szalay | A61K 35/35 |
| 11,285,194 | B2 | 3/2022 | Szalay et al. | 424/93.2 |
| 11,607,450 | B2 * | 3/2023 | Szalay | A61K 39/285 |
| 2004/0072775 | A1 | 4/2004 | Sobol et al. | 514/44 |
| 2007/0086984 | A1 | 4/2007 | Coffey et al. | 424/93.2 |
| 2008/0206201 | A1 | 8/2008 | Beier et al. | 424/93.6 |
| 2009/0162288 | A1 | 6/2009 | Chen et al. | 424/9.3 |
| 2009/0324616 | A1 | 12/2009 | Stassi et al. | 424/174.1 |
| 2010/0055102 | A1 | 3/2010 | Langermann | 424/174.1 |
| 2010/0297072 | A1 | 11/2010 | DePinho | 424/85.2 |
| 2011/0027239 | A1 | 2/2011 | Paek | 424/93.21 |
| 2011/0064650 | A1 | 3/2011 | Szalay | 424/1.11 |
| 2011/0171219 | A1 | 7/2011 | Merchant | 435/325 |
| 2012/0087901 | A1 | 4/2012 | Nelson | 424/93.21 |
| 2013/0273007 | A1 | 10/2013 | Szalay et al. | 424/93.2 |
| 2014/0017787 | A1 | 1/2014 | Betancourt | 435/375 |
| 2014/0271677 | A1 | 9/2014 | Palese et al. | 424/172.1 |
| 2015/0086541 | A1 | 3/2015 | Aguilar-Cordova | 424/133.1 |
| 2015/0352206 | A1 | 12/2015 | Gajewski et al. | 424/173.1 |

(Continued)

FOREIGN PATENT DOCUMENTS

| | | |
|---|---|---|
| WO | WO 2008/009115 | 1/2008 |
| WO | WO 2008/052054 | 5/2008 |

(Continued)

OTHER PUBLICATIONS

U.S. Appl. No. 16/676,413, filed Nov. 6, 2019, 2020-0140824, May 7, 2020.

(Continued)

*Primary Examiner* — Bao Q Li

(74) *Attorney, Agent, or Firm* — Womble Bond Dickinson (US) LLP; Stephanie Seidman

(57) ABSTRACT

Disclosed herein are methods and compositions related to therapy for cancer. More specifically, the disclosed methods and compositions are related to the use of smallpox vaccine to induce an effective anti-tumor immune response.

19 Claims, 1 Drawing Sheet

(56) References Cited

U.S. PATENT DOCUMENTS

Figure 1A:
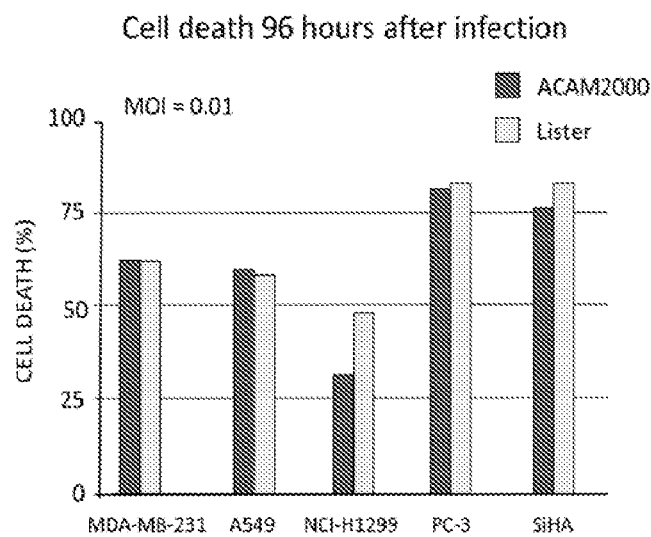

| | | | |
|---|---|---|---|
| 2017/0043010 A1 | 2/2017 | Szalay et al. | 424/186.1 |
| 2017/0239338 A1 | 8/2017 | Szalay et al. | 424/93.2 |
| 2018/0326048 A1 | 11/2018 | Szalay et al. | 424/186.1 |
| 2019/0367880 A1 | 12/2019 | Draganov | 424/93.21 |
| 2020/0318073 A9 | 10/2020 | Draganov et al. | 424/93.21 |
| 2021/0046178 A1 | 2/2021 | Szalay et al. | 424/232.1 |
| 2021/0060101 A1 | 3/2021 | Aboody et al. | 424/93.21 |
| 2022/0241388 A1 | 8/2022 | Szalay et al. | 424/93.2 |
| 2023/0022205 A1 | 1/2023 | Draganov et al. | 424/93.21 |

FOREIGN PATENT DOCUMENTS

| | | |
|---|---|---|
| WO | WO 2009/139921 | 11/2009 |
| WO | WO 2011/070974 | 6/2011 |
| WO | WO 2012/061120 | 5/2012 |
| WO | WO 2013/112942 | 8/2013 |
| WO | WO 2014/022138 | 2/2014 |
| WO | WO 2014/066834 | 5/2014 |
| WO | WO 2015/089280 | 6/2015 |
| WO | WO 2016/008976 | 1/2016 |
| WO | WO 2016/065330 | 4/2016 |
| WO | WO 2016/149559 | 9/2016 |
| WO | WO 2017/027757 | 2/2017 |
| WO | WO 2019/236633 | 12/2019 |
| WO | WO 2019/236633 | 3/2020 |
| WO | WO 2020/097269 | 5/2020 |
| WO | WO 2020/247385 | 12/2020 |

OTHER PUBLICATIONS

U.S. Appl. No. 17/689,643, filed Mar. 8, 2022, 2022-0241388, Aug. 4, 2022.

U.S. Appl. No. 17/952,565, filed Sep. 26, 2022, 2023-0022205, Jan. 26, 2023.

U.S. Appl. No. 18/295,171, filed Apr. 3, 2023.

Letter/Written Disclosure of the Information Disclosure Statement for the above-referenced application, filed herewith on Apr. 10, 2023, 2 pages.

Advani et al., "Viral Oncolysis." Holland-Frei Cancer Medicine. 6th Edition. Hamilton (ON): BC Decker (2003). Available from: <URL:ncbi.nlm.nih.gov/books/NBK13520/, 13 pages.

Ahmed et al., "A Comparative Study of Neural and Mesenchymal Stem Cell-Based Carriers for Oncolytic Adenovirus in a Model of Malignant Glioma," Mol. Pharm. 8(5):1559-1572 (2011).

Berglund et al., "Immunoprivileged no more: measuring the immunogenicity of allogeneic adult mesenchymal stem cells," Stem Cell Research & Therapy 8:288 (2017) [7 pages].

Bolontrade et al., "A specific subpopulation of mesenchymal stromal cell carriers overrides melanoma resistance to an oncolytic adenovirus," Stem cells and development 21(14): 2689-2702 (2012).

Bourin et al., "Stromal cells from the adipose tissue-derived stromal vascular fraction and culture expanded adipose tissue-derived stromal/stem cells: a joint statement of the International Federation for Adipose Therapeutics and Science (IFATS) and the International Society for Cellular Therapy (ISCT)," Cytotherapy 15(6):641-648 (2013).

Buckel et al., "Combination of fractionated irradiation with anti-VEGF expressing vaccinia virus therapy enhances tumor control by simultaneous radiosensitization of tumor associated endothelium," Int. J. Cancer 133: 2989-2999 (2013).

Cancer Facts and Figures American Cancer Society: Atlanta, GA (2008) (72 pages).

Casteilla et al., "Adipose-derived stromal cells: Their identity and uses in clinical trials, an update," World J. Stem Cells 3(4):25-33 (2011).

Cecil et al., "Vaccinia virus injected human tumors: oncolytic virus efficiency predicted by antigen profiling analysis fitted boolean models," Bioengineered 10(1):190-96 (2019).

W. M. Chan and G. McFadden, "Oncolytic Poxviruses," Annu. Rev. Virol. 1(1): 119-141 (2014).

Cho et al., "Role of Toll-Like Receptors on Human Adipose-Derived Stromal Cells," Stem Cells 24(12):2744-52 (2006).

Choi et al., "Correlation of computed tomography and positron emission tomography in patients with metastatic gastrointestinal stromal tumor treated at a single institution with imatinib mesylate: proposal of new computed tomography response criteria," J. Clin. Oncology 25(13): 1753-1759 (2007).

Deng et al., "Irradiation and anti-PD-L1 treatment synergistically promote antitumor immunity in mice," J. Clin. Invest. 124(2): 687-695 (2014).

De Souza Trindade et al., "Real-time PCR assay to identify variants of Vaccinia virus: implications for the diagnosis of bovine vaccinia in Brazil," J. Virol. Methods 152(1-2):63-71 (2008).

Dias et al., "Targeted Cancer Immunotherapy With Oncolytic Adenovirus Coding for a Fully Human Monoclonal Antibody Specific for CTLA-4," Gene Ther. 19(10):988-98 (2012).

Draganov et al., "Delivery of oncolytic vaccinia virus by matched allogeneic stem cells overcomes critical innate and adaptive immune barriers," J. Transl. Med. 17(1):100 (2019), 22 pages.

Draghiciu et al., "Therapeutic immunization and local low-dose tumor irradiation, a reinforcing combination," Int. J. Cancer 134: 859-872 (2014).

Fares et al., "Neural stem cell delivery of an oncolytic adenovirus in newly diagnosed malignant glioma: a first-in-human, phase 1, dose-escalation trial," Lancet Oncol. 22:1103-1114 (2021).

Frentzen et al., "Anti-VEGF single-chain antibody GLAF-1 encoded by oncolytic vaccinia virus significantly enhances antitumor therapy," Proc. Natl. Acad. Sci. 106(31):12915-12920 (2009).

Gao et al., "Recombinant Vesicular Stomatitis Virus Targeted to Her2/neu Combined With anti-CTLA4 Antibody Eliminates Implanted Mammary Tumors," Cancer Gene Ther 16(1):44-52 (2009).

Guo et al., "The combination of immunosuppression and carrier cells significantly enhances the efficacy of oncolytic poxvirus in the pre-immunized host," Gene Ther. 17(12):1465-1475 (2010).

Guse et al., "Oncolytic vaccinia virus for the treatment of cancer," Expert Opin. Biol. Ther. 11(5):595-608 (2011).

Hamid et al., Abstract No. 9010, entitled "Clinical activity, safety, and biomarkers of MPDL3280A, an engineered PD-L1 antibody in patients with locally advanced or metastatic melanoma (mM)," Journal of Clinical Oncology 31(15_suppl):9010-9010. Doi: 10.1200/jco.2013.31.15_suppl.9010. Published on May 20, 2013 [online]; retrieved on Apr. 6, 2021, from: <URL:ascopubs.org/doi/abs/10.1200/jco.2013.31.15_suppl.9010, 3 pages.

Hang-Fu et al., "Liposuction Fat-Fillant Implant for Breast Augmentation and Reconstruction," Aesthetic Plastic Surgery 19(5): 427-437 (1995).

Huang, T., "Vaccinia Virus-mediated Therapy of Solid Tumor Xenografts: Intra-tumoral Delivery of Therapeutic Antibodies," Dissertation (2013), 172 pages.

Huang et al., "The use of hypoxic cultured mesenchymal stem cell for oncolytic virus therapy," Cancer Gene Therapy 20:308-316 (2013).

Iovino et al., "Immunotherapy targeting colon cancer stem cells," Immunotherapy 3(1):97-106 (2011).

John et al., "Oncolytic Virus and Anti-4-1BB Combination Therapy Elicits Strong Antitumor Immunity against Established Cancer," Cancer Research 72(7):1651-1660 (2012).

Josiah et al., "Adipose-derived Stem Cells as Therapeutic Delivery Vehicles of an Oncolytic Virus for Glioblastoma," Mol. Ther. 18(2): 377-85 (2010).

Kang et al., "Neurogenesis of Rhesus adipose stromal cells," J. Cell Sci. 117(18):4289-4299 (2004).

Kerrigan et al., "Mesenchymal stem cells for the delivery of oncolytic viruses in gliomas," Cytotherapy 19(4):445-457 (2017).

Kilinc et al., "Colonization of xenograft tumors by oncolytic vaccinia virus (VACV) results in enhanced tumor killing due to the involvement of myeloid cells," J. Transl. Med. 14(1):340 (2016), 12 pages.

Kilinc et al., "The ratio of ADSCs to HSC-progenitors in adipose tissue derived SVF may provide the key to predict the outcome of stem-cell therapy," Clin. Transl. Med. 7:5 (2018), 20 pages.

(56) References Cited

OTHER PUBLICATIONS

Kim et al., "Stem Cell-Based Cell Carrier for Targeted Oncolytic Virotherapy: Translational Opportunity and Open Questions," Viruses 7(12): 6200-6217 (2015).
Kurita et al., "Influences of centrifugation on cells and tissues in liposuction aspirates: optimized centrifugation for lipotransfer and cell isolation," Plastic and Reconstructive Surgery 121(3): 1033-1041 (2008).
Lamfers et al., "Homing properties of adipose-derived stem cells to intracerebral glioma and the effects of adenovirus infection," Cancer Lett. 274(1):78-87 (2009).
Lauer et al., "Phase I Study of Oncolytic Vaccinia Virus GL-ONC1 in Patients with Peritoneal Carcinomatosis," Clin. Cancer Res. 24(18):4388-4398 (2018).
Lesterhuis et al., "Synergistic Effect of CTLA-4 Blockade and Cancer Chemotherapy in the Induction of Anti-Tumor Immunity," PLoS One 8(4):e61895 (2013), 8 pages.
Li et al., "Adjuvant effect of anti-4-1BB mAb administration in adoptive T cell therapy of cancer," Int. J. Biol. Sci. 3(7):455-462 (2007).
Lombardo et al., "Toll-Like Receptor-Mediated Signaling in Human Adipose-Derived Stem Cells: Implications for Immunogenicity and Immunosuppressive Potential," Tissue Eng.: Part A 15:1579-1589 (2009).
Lu et al., "Genetic engineering of dendritic cells to express immunosuppressive molecules (viral IL-10, TGF-β, and CTLA4Ig)," J. Leukoc. Biol. 66(2):293-296 (1999).
Mader et al., "Mesenchymal stem cell carriers protect oncolytic measles viruses from antibody neutralization in an orthotopic ovarian cancer therapy model," Clin. Cancer Res. 15(23):7246-7255 (2009).
Mader et al., "Optimizing patient derived mesenchymal stem cells as virus carriers for a Phase I clinical trial in ovarian cancer," J. Trans. Med. 11:20 (2013), 14 pages.
Martinez-Quintanilla et al., "Encapsulated stem cells loaded with hyaluronidase-expressing oncolytic virus for brain tumor therapy," Mol. Ther. 23(1):108-118 (2015).
Mell et al., "Phase I Trial of Intravenous Oncolytic Vaccinia Virus (GL-ONC1) with Cisplatin and Radiotherapy in Patients with Locoregionally Advanced Head and Neck Carcinoma," Clin. Cancer Res. 23(19):5696-5702 (2017).
Minev et al., "First-in-human study of TK-positive oncolytic vaccinia virus delivered by adipose stromal vascular fraction cells," Transl. Med. 17(1):271 (2019), 15 pages.
Moreno et al., "Human Menstrual Blood-Derived Mesenchymal Stem Cells as Potential Cell Carriers for Oncolytic Adenovirus," Stem Cells International 2017:3615729 (2017), 10 pages.
Msaouel et al., "Oncolytic measles virus strains as novel anticancer agents," Expert Opin. Biol. Ther. 13(4):483-502 (2013).
Munguia et al., "Cell carriers to deliver oncolytic viruses to sites of myeloma tumor growth," Gene Ther. 15(10):797-806 (2008).
Nakashima et al., "Directing systemic oncolytic viral delivery to tumors via carrier cells." Cytokine Growth Factor Reviews 21(2-3):119-126 (2010).
Nishio et al., "Armed oncolytic virus enhances immune functions of chimeric antigen receptor-modified T cells in solid tumors," Cancer Res. 74(18):5195-5205 (2014).
Patil et al., "Virotherapy of canine tumors with oncolytic vaccinia virus GLV-1h109 expressing an anti-VEGF single-chain antibody," PLoS One 7(10):e47472 (2012).
Payne et al., "Human adipose-derived mesenchymal stem cells engineered to secrete IL-10 inhibit APC function and limit CNS autoimmunity," Brain, Behavior, and Immunity 30(1):103-114 (2013).
Petrov et al., "Canine Adipose-Derived Mesenchymal Stem Cells (cAdMSCs) as a "Trojan Horse" in Vaccinia Virus Mediated Oncolytic Therapy against Canine Soft Tissue Sarcomas," Viruses 12(7):750 (2020), 13 pages.
Power, A.T. and J.C. Bell, "Cell-based Delivery of Oncolytic Viruses: A New Strategic Alliance for a Biological Strike Against Cancer," Mol. Ther. 15(4):660-665 (2007).

Protest Documents Submitted Under 37 CFR § 1.99 on Aug. 5, 2009 in connection with U.S. Appl. No. 12/218,953, 53 pages.
Ramirez et al., "Patient-derived mesenchymal stem cells as delivery vehicles for oncolytic virotherapy: novel state-of-the-art technology," Oncolytic Virotherapy 4:149-155 (2015).
Response, filed Aug. 17, 2009, to Third Party Submission of Protest Documents Submitted Under 37 CFR § 1.99 on Aug. 5, 2009 in connection with U.S. Appl. No. 12/218,953, 5 pages.
Rincon et al., "Mesenchymal Stem Cell Carriers Enhance Antitumor Efficacy of Oncolytic Adenoviruses in an Immunocompetent Mouse Model," Oncotarget 8(28):45415-45431 (2017).
Roy, D. G. and J. C. Bell, "Cell carriers for oncolytic viruses: current challenges and future directions," Oncolytic Virother. 2:47-56 (2013).
Quetglas et al., "Immunotherapeutic synergy between anti-CD137 mAb and intratumoral administration of a cytopathic Semliki Forest virus encoding IL-12," Mol. Ther. 20(9):1664-1675 (2012).
Studeny et al., "Mesenchymal Stem Cells: Potential Precursors for Tumor Stroma and Targeted-Delivery Vehicles for Anticancer Agents," J. Natl. Cancer Inst. 96(21):1593-1603 (2004).
Thorne et al., "Vaccinia virus and oncolytic virotherapy of cancer," Curr. Opin. Mol. Ther. 7(4):359-365 (2005).
Thorne et al., "Targeting localized immune suppression within the tumor through repeat cycles of immune cell-oncolytic virus combination therapy," Molecular Therapy 18(9): 1698-1705 (2010).
Tsoneva et al., "Humanized Mice with Subcutaneous Human Solid Tumors for Immune Response Analysis of Vaccinia Virus-Mediated Oncolysis," Mol. Ther. Oncolytics 5:41-61 (2017).
Verardi et al., "A vaccinia virus renaissance: New vaccine and immunotherapeutic uses after smallpox eradication," Human Vaccines & Immunotherapeutics 8(7):961-970 (2012).
Walsh, Stephen R., and Raphael Dolin. "Vaccinia viruses: vaccines against smallpox and vectors against infectious diseases and tumors." Expert Rev. Vaccines 10(8):1221-40 (2011).
Wang et al., "Oncolytic vaccinia virus GLV-1h68 strain shows enhanced replication in human breast cancer stem-like cells in comparison to breast cancer cells," J. Transl. Med. 10:167 (2012), 15 pages.
Wang et al., "Optical detection and virotherapy of live metastatic tumor cells in body fluids with vaccinia strains," PLoS One 8(9):e71105 (2013), 12 pages.
Wang et al., "The Synergistic In Vitro and In Vivo Antitumor Effect of Combination Therapy with Salinomycin and 5-Fluorouracil against Hepatocellular Carcinoma," PLoS One 9(5):e97414 (2014), 10 pages.
Waterman et al., "A New Mesenchymal Stem Cell (MSC) Paradigm: Polarization into a Pro-Inflammatory MSC1 or an Immunosuppressive MSC2 Phenotype," PLoS One 5(4):e10088 (2010), 14 pages.
Willmon et al., "Cell carriers for oncolytic viruses: Fed Ex for cancer therapy," Molecular Therapy 17(10):1667-1676 (2009).
Wolchok et al., "Guidelines for the evaluation of immune therapy activity in solid tumors: immune-related response criteria," Clinical Cancer Research 15(23):7412-7420 (2009).
Yang et al., "Adult neural stem cells expressing IL-10 confer potent immunomodulation and remyelination in experimental autoimmune encephalitis," J. Clin. Invest. 119(12):3678-3691 (2009).
Yokouchi et al., "Anti-OX40 monoclonal antibody therapy in combination with radiotherapy results in therapeutic antitumor immunity to murine lung cancer," Cancer Sci. 99(2):361-367 (2008).
Yoshimura et al., "Cell-assisted lipotransfer for cosmetic breast augmentation: supportive use of adipose-derived stem/stromal cells," Aesthetic Plastic Surgery 32(1):48-55 (2008).
Yuan et al., "Interleukin-23-Expressing Bone Marrow-Derived Neural Stem-Like Cells Exhibit Antitumor Activity Against Intracranial Glioma," Cancer Research 66(5): 2630-2638 (2006).
Zamarin et al., "Localized Oncolytic Virotherapy Overcomes Systemic Tumor Resistance to Immune Checkpoint Blockade Immunotherapy," Sci. Trans. Med. 6(226):226ra32, 14 pages.
Zeh et al., "First-in-man study of western reserve strain oncolytic vaccinia virus: safety, systemic spread, and antitumor activity," Mol. Ther. 23(1):202-214 (2015).

(56) References Cited

OTHER PUBLICATIONS

Zhang et al., "Eradication of solid human breast tumors in nude mice with an intravenously injected light-emitting oncolytic vaccinia virus," Cancer Research 67(20):10038-10046 (2007).
Minev et al., "First in man study of TK positive oncolytic vaccinia virus delivered by adipose stromal vascular fraction cells," [abstract] Journal for Immuno Therapy of Cancer, 6(Suppl 1):115, Abstract No. P609, Nov. 2018, 2 pages.
Minev et al., "First in man study of TK positive oncolytic vaccinia virus delivered by adipose stromal vascular fraction cells," poster presented at The Society for Immunotherapy of Cancer's (SITC) 33rd Annual Meeting | Nov. 7-11, 2018 Washington, D.C., 1 page.
Nguyen et al., "A cell-based platform to potentiate oncolytic virus therapies," poster presented at ASCO-SITC Clinical Immuno-Oncology Symposium Feb. 6-8, 2020 Orlando, Florida, 1 page.
Nguyen et al., "A cell-based platform to potentiate oncolytic virus: Potential approach for cancer therapies," abstract presented at ASCO-SITC Clinical Immuno-Oncology Symposium Feb. 6, 2020 Orlando, Florida, Abstract No. 21, 2 pages.
Santidrian et al., "A cell-based platform to protect and enhance oncolytic virus therapies," [abstract] Journal for Immuno Therapy of Cancer, 6(Suppl 1):115, Abstract No. P617, Nov. 2018, 1 page.
Santidrian et al., "A cell-based platform to potentiate oncolytic virus therapies," poster presented at The Society for Immunotherapy of Cancer's (SITC) 33rd Annual Meeting | Nov. 7-11, 2018 Washington, D.C., 1 page.
News Release, Calidi Biotherapeutics "Calidi Biotherapeutics Announces Two Abstracts Accepted for Presentation at the Society for Immunotherapy of Cancer's (SITC) 33rd Annual Meeting." Published Nov. 6, 2018 [online] Retrieved from: <URL: calidibio.com/2018/11/06/calidi-biotherapeutics-inc-granted-new-patent-from-USPTO-for-cell-based-delivery-of-oncolytic-vaccinia-viruses-2/ [retrieved on Nov. 29, 2018], 3 pages.
News Release, "Calidi Biotherapeutics Announces A Collaborative Study With The National Institutes Of Health (NIH) On The Therapeutic Potential Of Oncolytic Viruses Delivered By Mesenchymal Stem Cells," Published May 28, 2019 [online] Retrieved from: <URL: prnewswire.com/news-releases/calidi-biotherapeutics-announces-a-collaborative-study-with-the-national-institutes-of-health-nih-on-the-therapeutic-potential-of-oncolytic-viruscs-delivered-by-mesenchymal-stem-cells-300857135.html [retrieved on May 28, 2019], 3 pages.
News Release, "Calidi Biotherapeutics Presents Data at the 2020 ASCO-SITC Clinical Immuno-Oncology Symposium," Published Feb. 13, 2020 [online] Retrieved from: <URL: calidibio.com/2020/02/13/calidi-biotherapeutics-presents-data-at-the-2020-asco-sitc-clinical-immuno-oncology-symposium/ [retrieved on Mar. 11, 2020], 4 pages.
News Release, entitled "Calidi Biotherapeutics Announces Partnership with GenScript ProBio for Distribution of its SuperNova-1 Technology." Published Jun. 8, 2021 [online]; retrieved on Jun. 16, 2021, from: <URL:businesswire.com/news/home/20210608005504/en/Calidi-Biotherapeutics-Announces-Partnership-with-GenScript-ProBio-for-Distribution-of-its-SuperNova-1-Technology, 2 pages.
News Release, entitled "Calidi Biotherapeutics Announces Agreement with Northwestern University for Exclusive Commercial Rights to their IND for Treatment of Malignant Glioma." Published Aug. 4, 2021 [online]; retrieved on Oct. 6, 2021, from: <URL:calidibio.com/2021/08/04/calidi-biotherapeutics-announces-agreement-with-northwestern-university-for-exclusive-commercial-rights-to-their-ind-for-treatment-of-malignant-glioma, 4 pages.
News Release, entitled "Calidi Biotherapeutics Announces Exclusive License Agreement with City of Hope and the University of Chicago for Novel Oncolytic Virotherapy Technology." Published Aug. 16, 2021 [online]; retrieved on Oct. 6, 2021, from: <URL:calidibio.com/2021/08/16/calidi-biotherapeutics-announces-exclusive-license-agreement-with-city-of-hope-and-the-university-of-chicago-for-novel-oncolytic-virotherapy-technology, 5 pages.
News Release, entitled "Calidi Biotherapeutics Announces Dr. Maciej S. Lesniak Presentation at 13th International Oncolytic Virotherapy Conference." Published Nov. 5, 2021 [online]; retrieved on Jan. 25, 2022, from: <URL:calidibio.com/2021/11/05/calidi-biotherapeutics-announces-dr-maciej-s-lesniak-presentation-at-13th-international-oncolytic-virotherapy-conference/, 3 pages.
International Search Report and Written Opinion, mailed Jan. 14, 2016, in connection with International Patent Application No. PCT/US2015/057234, 8 pages.
International Preliminary Report on Patentability, issued Apr. 25, 2017, in connection with International Patent Application No. PCT/US2015/057234, 5 pages.
International Preliminary Report on Patentability, issued May 4, 2017, in connection with International Patent Application No. PCT/US2015/057234, 6 pages.
Office Action, mailed May 1, 2018, in connection with U.S. Appl. No. 15/521,602, 25 pages.
Response, filed May 24, 2018, to Office Action, mailed May 1, 2018, in connection with U.S. Appl. No. 15/521,602, 9 pages.
Office Action, issued Aug. 29, 2018, in connection with U.S. Appl. No. 15/521,602, 14 pages.
Amendment and Request for Continued Examination, filed Nov. 29, 2018, responsive to Office Action, mailed Aug. 29, 2018, in connection with U.S. Appl. No. 15/521,602 [Amendment, response and inventor declaration], 42 pages.
Office Action, mailed Mar. 18, 2019, in connection with U.S. Appl. No. 15/521,602, 20 pages.
Response, filed Jul. 18, 2019, to Office Action, mailed Mar. 18, 2019, in connection with U.S. Appl. No. 15/521,602, 32 pages.
Office Action, mailed Oct. 22, 2019, in connection with U.S. Appl. No. 15/521,602, 30 pages.
Response and Request for Continued Examination, filed Feb. 10, 2020, responsive to Office Action, mailed Oct. 22, 2019, in connection with U.S. Appl. No. 15/521,602, 48 pages.
Office Action, mailed Jul. 6, 2020, in connection with U.S. Appl. No. 15/521,602, 51 pages.
Response, filed Jan. 6, 2021, responsive to Office Action, mailed Jul. 6, 2020, in connection with U.S. Appl. No. 15/521,602, 71 pages.
Final Office Action, issued Apr. 6, 2021, in connection with U.S. Appl. No. 15/521,602, 14 pages.
Response, filed Oct. 6, 2021, to Office Action, issued Apr. 6, 2021, in connection with U.S. Appl. No. 15/521,602, 17 pages.
Notice of Allowance, issued Nov. 19, 2021, in connection with U.S. Appl. No. 15/521,602, 7 pages.
Examiner's Report, issued Apr. 5, 2019, in connection with Australian Patent Application No. 2015335607, 3 pages.
Response, filed Oct. 23, 2019, to Examiner's Report, issued Apr. 5, 2019, in connection with Australian Patent Application No. 2015335607, 19 pages.
Examiner's Report, issued Oct. 25, 2019, in connection with Australian Patent Application No. 2015335607, 3 pages.
Response, filed Mar. 10, 2020, to Examiner's Report, issued Oct. 25, 2019, in connection with Australian Patent Application No. 2015335607, 19 pages.
Examiner's Report, issued Mar. 12, 2020, in connection with Australian Patent Application No. 2015335607, 5 pages.
Response, filed Mar. 26, 2020, to Examiner's Report, issued Mar. 12, 2020, in connection with Australian Patent Application No. 2015335607, 18 pages.
Notice of Acceptance, issued Apr. 8, 2020, in connection with Australian Patent Application No. 2015335607, 3 pages.
Preliminary Office Action, issued Oct. 2, 2020, in connection with Brazilian Patent Application No. BR112017008399-0 [English translation and original document in Portuguese], 6 pages.
Examiner's Report, issued Nov. 22, 2018, in connection with Canadian Patent Application No. 3,003,133, 6 pages.
Response, filed Feb. 22, 2019, to Examiner's Report, issued Nov. 22, 2018, in connection with Canadian Patent Application No. 3,003,133, 60 pages.
Examiner's Report, issued Mar. 26, 2019, in connection with Canadian Patent Application No. 3,003,133, 5 pages.
Response, filed Jun. 21, 2019, Examiner's Report, issued Mar. 26, 2019, in connection with Canadian Patent Application No. 3,003,133, 36 pages.

(56) References Cited

OTHER PUBLICATIONS

Examiner's Report, issued Sep. 6, 2019, in connection with Canadian Patent Application No. 3,003,133, 6 pages.
Response, filed Dec. 6, 2019, to Examiner's Report, issued Sep. 6, 2019, in connection with Canadian Patent Application No. 3,003,133, 83 pages.
Notice of Allowance, issued Apr. 9, 2020, in connection with Canadian Patent Application No. 3,003,133, 1 page.
Supplementary European Search Report, dated May 23, 2018, issued in connection with corresponding European Patent Application No. 15852615.2, 7 pages.
Response, filed Oct. 22, 2018, to Communication pursuant to Rules 70(2) and 70a(2) EPC, issued Jun. 8, 2018, issued in connection with corresponding European Patent Application No. 15852615.2, 6 pages.
Communication Pursuant to Article 94(3) EPC, issued Feb. 7, 2019, in connection with European Patent Application No. 15852615.2, 4 pages.
Response, filed Apr. 10, 2019, to Communication Pursuant to Article 94(3) EPC, issued Feb. 7, 2019, in connection with European Patent Application No. 15852615.2, 51 pages.
Communication Pursuant to Article 94(3) EPC, issued Jun. 27, 2019, in connection with European Patent Application No. 15852615.2 [D1=US 2010/0297072], 5 pages.
Response, filed Oct. 7, 2019, to Communication Pursuant to Article 94(3) EPC, issued Jun. 27, 2019, in connection with European Patent Application No. 15852615.2, 20 pages.
Communication Pursuant to Article 94(3) EPC [claims deemed allowable], issued Jan. 7, 2020, in connection with European Patent Application No. 15852615.2 [D1=US 2010/0297072], 4 pages.
Response, filed Apr. 17, 2020, to Communication Pursuant to Article 94(3) EPC, issued Jan. 7, 2020, in connection with European Patent Application No. 15852615.2, 46 pages.
Communication Pursuant to Rule 71(3) EPC (Notice of Allowance), issued Jun. 12, 2020, in connection with European Patent Application No. 15852615.2, 7 pages.
Certificate of Grant, issued Nov. 25, 2020, in connection with European Patent Application No. 15852615.2, 1 page.
Office Action, issued Jul. 1, 2019, in connection with Israel Application No. 251890 [Original document in Hebrew and English translation], 4 pages.
Response, filed Oct. 3, 2019, to Office Action, issued Jul. 1, 2019, in connection with Isracl Application No. 251890 [English translation and English claims and original document as-filed in Hebrew], 14 pages.
Notification Prior to Acceptance, issued Oct. 27, 2019, in connection with Israel Application No. 251890 [Original document in Hebrew, English translation, and accepted claims in English], 11 pages.
Office Action, dated Jan. 22, 2021, issued in connection with Mexican Patent Application No. MX/a/2017/005325 [English translation, and original document in Spanish], 8 pages.
Response, filed Mar. 19, 2021, to Office Action, dated Jan. 22, 2021, issued in connection with Mexican Patent Application No. MX/a/2017/005325 [English instructions for Response; and original Response as filed in Spanish], 33 pages.
Office Action, dated Jun. 2, 2021, issued in connection with Mexican Patent Application No. MX/a/2017/005325 [English translation, and original document in Spanish], 8 pages.
Response, filed Nov. 11, 2021, to Office Action, dated Jun. 2, 2021, issued in connection with Mexican Patent Application No. MX/a/2017/005325 [English instructions and document as-filed in Spanish], 31 pages.
Notice of Allowance, dated Nov. 24, 2021, in connection with Mexican Patent Application No. MX/a/2017/005325 [machine-generated English translation and original document as issued in Spanish], 4 pages.
Examination Report, issued Apr. 18, 2019, in connection with New Zealand Patent Application No. 732211, 5 pages.
Response, filed Sep. 29, 2019, to Examination Report, issued Apr. 18, 2019, in connection with New Zealand Patent Application No. 732211, 54 pages.
Examination Report, issued Oct. 31, 2019, in connection with New Zealand Patent Application No. 732211, 5 pages.
Response, filed Jan. 29, 2020, to Examination Report, issued Oct. 31, 2019, in connection with New Zealand Patent Application No. 732211, 10 pages.
Examination Report (claims accepted), issued Feb. 5, 2020, in connection with New Zealand Patent Application No. 732211, 1 page.
English letter, dated Jun. 20, 2019, reporting Official Action, issued May 24, 2019, in connection with Russian Application No. 2017117889 [English letter and origianl document in Russian], 11 pages.
Response, filed Oct. 11, 2019, to Official Action, issued May 24, 2019, in connection with Russian Application No. 2017117889 [English instructions, and Response and claims as-filed, in Russian], 74 pages.
English letter, dated Dec. 11, 2019, reporting Decision to Grant, issued Oct. 18, 2019, in connection with Russian Application No. 2017117889 [English letter and origianl document in Russian], 14 pages.
Search Report and Written Opinion, issued Apr. 6, 2018, in connection with Singaporean Patent Application No. 11201703326S, 11 pages.
Response, filed Aug. 29, 2018, to Search Report and Written Opinion, issued Apr. 6, 2018, in connection with Singaporean Patent Application No. 11201703326S, 23 pages.
Written Opinion, issued May 9, 2019, in connection with Singaporean Patent Application No. 11201703326S, 9 pages.
Response, filed Oct. 3, 2019, to Written Opinion, issued May 9, 2019, in connection with Singaporean Patent Application No. 11201703326S, 47 pages.
Examination Report, issued Oct. 28, 2020, and Notice of Eligibility for Grant, issued Oct. 29, 2020, in connection with Singaporean Patent Application No. 11201703326S, 6 pages.
International Preliminary Report on Patentability, issued Sep. 28, 2017, in connection with International Patent Publication No. PCT/US2016/022978, 10 pages.
International Search Report and Written Opinion, issued Jul. 27, 2016, in connection with International Patent Publication No. PCT/US2016/022978, 12 pages.
Office Action, mailed Dec. 1, 2017, in connection with U.S. Appl. No. 15/235,082, 8 pages.
Response, filed Mar. 1, 2018, to Office Action, mailed Dec. 1, 2017, in connection with U.S. Appl. No. 15/235,082, 8 pages.
Notice of Allowance, mailed May 1, 2018, in connection with U.S. Appl. No. 15/235,082, 8 pages.
Updated Notice of Allowance, mailed Aug. 21, 2018, in connection with U.S. Appl. No. 15/235,082, 6 pages.
Office Action, mailed Mar. 19, 2020, in connection with U.S. Appl. No. 16/044,136, 6 pages.
Response, filed May 12, 2020, to Office Action, mailed Mar. 19, 2020, in connection with U.S. Appl. No. 16/044,136, 8 pages.
Notice of Allowance, mailed Jul. 29, 2020, in connection with U.S. Appl. No. 16/044,136, 8 pages.
Corrected Notice of Allowability, mailed Sep. 18, 2020, in connection with U.S. Appl. No. 16/044,136, 4 pages.
Corrected Notice of Allowability, mailed Oct. 15, 2020, in connection with U.S. Appl. No. 16/044,136, 5 pages.
Office Action, issued May 12, 2022, in connection with U.S. Appl. No. 17/089,527, 32 pages.
Response, filed Jun. 29, 2022, to Office Action, issued May 12, 2022, in connection with U.S. Appl. No. 17/089,527, 7 pages.
Final Office Action, issued Aug. 31, 2022, in connection with U.S. Appl. No. 17/089,527, 6 pages.
Response, filed Oct. 6, 2022, to Final Office Action, issued Aug. 31, 2022, in connection with U.S. Appl. No. 17/089,527, 10 pages.
Notice of Allowance, mailed Nov. 3, 2022, in connection with U.S. Appl. No. 17/089,527, 10 pages.
International Search Report and Written Opinion, issued Feb. 6, 2017, in connection with International Patent Application No. PCT/US2016/046647, 14 pages.

(56) References Cited

OTHER PUBLICATIONS

International Preliminary Report on Patentability, issued Feb. 13, 2018, in connection with International Patent Application No. PCT/US2016/046647, 10 pages.
Examiner's Report, issued Jun. 19, 2019, in connection with Canadian Application No. 3,004,891, 5 pages.
Reponse, filed Sep. 17, 2019, to Examiner's Report, issued Jun. 19, 2019, in connection with Canadian Application No. 3,004,891, 42 pages.
Notice of Allowance, mailed Nov. 4, 2019, in connection with Canadian Application No. 3,004,891, 1 page.
Office Action, issued Jan. 4, 2021, in connection with Chinese Patent Application No. 201680058874.X [English translation, and original document as issued in Chinese], 12 pages.
Response, filed May 19, 2021, to Office Action, issued Jan. 4, 2021, in connection with Chinese Patent Application No. 201680058874.X [English language instructions for response; original documents as filed in Chinese; and English translation of amended claims], 28 pages.
Office Action, issued Oct. 11, 2021, in connection with Chinese Patent Application No. 201680058874.X [English translation, original document as issued in Chinese, and Pending Claims], 7 pages.
Response, filed Feb. 28, 2022, and Supplemental Response, filed Mar. 3, 2022, to Office Action, issued Oct. 11, 2021, in connection with Chinese Patent Application No. 201680058874.X [English language instructions for response; English translation of amended claims; original documents as filed in Chinese], 26 pages.
Notification of Granting a Patent Right, issued Mar. 30, 2022, in connection with Chinese Patent Application No. 201680058874.X [English language translation; original documents as issued in Chinese], 4 pages.
Letter, dated Jul. 15, 2020, reporting Official Action, issued May 12, 2020, in connection with Eurasian Patent Application No. 201800148 [Letter in English and Document as-issued in Russian], 4 pages.
Reponse, filed Oct. 22, 2020, to Office Action, issued May 12, 2020, in connection with Eurasian Patent Application No. 201800148 [English Instructions for Response, Response as-filed in Russian, and copy of reference cited in Response], 60 pages.
Office Action, dated Feb. 4, 2021, issued in connection with Eurasian Patent Application No. 201800148 [Reporting letter, dated Feb. 17, 2021, providing an English translation of the Office Action; and copy of the original Office Action as issued in Russian], 4 pages.
Response, filed Aug. 13, 2021, to Office Action, dated Feb. 4, 2021, issued in connection with Eurasian Patent Application No. 201800148 [English Instructions for Response and Response as filed in Russian], 25 pages.
Letter, dated Dec. 15, 2021, reporting Notification of Grant, issued in connection with Eurasian Patent Application No. 201800148, 1 page.
Communication Pursuant to Rules 161(1) and 162, dated Mar. 22, 2018, issued in connection with European Patent Application No. 16754618.3, 3 pages.
Response, filed Aug. 22, 2018, to Communication Pursuant to Rules 161(1) and 162, dated Mar. 22, 2018, issued in connection with European Patent Application No. 16754618.3, 5 pages.
Examination Report, issued Jul. 30, 2019, in connection with European Patent Application No. 16754618.3, 9 pages.
Response, filed Feb. 6, 2020, to Examination Report, issued Jul. 30, 2019, in connection with European Patent Application No. 16754618.3, 15 pages.
Examination Report, issued Jul. 29, 2020, in connection with European Patent Application No. 16754618.3, 5 pages.
Response, filed Dec. 3, 2020, to Examination Report, issued Jul. 29, 2020, in connection with European Patent Application No. 16754618.3, 80 pages.
Office Action, issued Dec. 3, 2019, in connection with Japanese Patent Application No. 2018-507579 [English translation and original document in Japanese], 7 pages.
Response, filed Mar. 2, 2020 to Office Action, issued Dec. 3, 2019, in connection with Japanese Patent Application No. 2018-507579 [English instructions for Response, documents as-filed in Japanese, and English translation of claims as-filed], 41 pages.
Office Action, issued Mar. 17, 2020, in connection with Japanese Patent Application No. 2018-507579 [English translation and original document in Japanese], 5 pages.
Response, filed Jun. 9, 2020, to Office Action, issued Mar. 17, 2020, in connection with Japanese Patent Application No. 2018-507579 [English instructions for Response, documents as-filed in Japanese, and English translation of claims as-filed], 16 pages.
Office Action, issued Jun. 23, 2020, in connection with Japanese Patent Application No. 2018-507579 [English translation and original document in Japanese], 7 pages.
Response, filed Sep. 18, 2020, to Office Action, issued Jun. 23, 2020, in connection with Japanese Patent Application No. 2018-507579 [English instructions for Response, and documents as-filed in Japanese], 14 pages.
Decision to Grant, issued Oct. 6, 2020, in connection with Japanese Patent Application No. 2018-507579 [English letter reporting Decision to Grant and original document in Japanese], 5 pages.
Office Action, issued Mar. 16, 2020, in connection with Korean Patent Application No. 10-2018-7007019 [English translation and original document in Korean], 13 pages.
Response, filed May 11, 2020, to Office Action, issued Mar. 16, 2020, in connection with Korean Patent Application No. 10-2018-7007019 [English instructions, document as-filed in Korean, and English translation of claims as-filed], 90 pages.
Decision to Grant, issued Oct. 13, 2020, in connection with Korean Patent Application No. 10-2018-7007019 [English translation and original document in Korean], 3 pages.
Letters Patent, issued Jan. 5, 2021, in connection with Korean Patent Application No. 10-2018-7007019 [English translation and original document in Korean], 3 pages.
Office Action, issued Jun. 3, 2021, in connection with Mexican Patent Application No. MX/a/2018/001755 [English translation and original document in Spanish], 8 pages.
Response, filed Nov. 11, 2021, to Office Action, issued Jun. 3, 2021, in connection with Mexican Patent Application No. MX/a/2018/001755 [English instructions and document as-filed in Spanish], 31 pages.
Office Action, issued Nov. 18, 2021, in connection with Mexican Patent Application No. MX/a/2018/001755 [English translation and original document in Spanish], 8 pages.
Response, filed Mar. 24, 2022, to Office Action, issued Nov. 18, 2021, in connection with Mexican Patent Application No. MX/a/2018/001755 [English instructions and document as-filed in Spanish], 19 pages.
Notice of Allowance, dated Apr. 1, 2022, in connection with Mexican Patent Application No. MX/a/2018/001755 [machine-generated English translation and original document as issued in Spanish], 4 pages.
Search Report and Written Opinion, issued Apr. 23, 2019, in connection with Singapore Patent Application No. 11201801177T, 11 pages.
Response, filed Sep. 23, 2019, to Search Report and Written Opinion, issued Apr. 23, 2019, in connection with Singapore Patent Application No. 11201801177T, 47 pages.
Examination Report [claims deemed allowable], issued Jul. 6, 2020, in connection with Singapore Patent Application No. 11201801177T, 4 pages.
Notice of Eligibility for Grant, issued Jul. 13, 2020, in connection with Singapore Patent Application No. 11201801177T, 1 page.
Certificate of Grant, issued Mar. 29, 2021, in connection with Singapore Patent Application No. 11201801177T, 2 pages.
Letter/Written Disclosure of the Supplemental Information Disclosure Statement for the above-referenced application, filed herewith on Apr. 19, 2024, 3 pages.
Office Action, published Mar. 5, 2024, in connection with Brazilian Patent Application No. BR122021017877-1 [English language translation and original document in Portuguese], 23 pages.

\* cited by examiner

Oncolysis of a panel of human tumor cell lines after infection with ACAM2000 and Lister virus strains

SMALLPOX VACCINE FOR CANCER TREATMENT

CROSS-REFERENCE TO RELATED APPLICATIONS

This application is a continuation of allowed U.S. application Ser. No. 17/089,527 entitled "SMALLPDX VACCINE FOR CANCER TREATMENT," filed Nov. 4, 2020, to inventors Aladar A. Szalay and Boris Minev, which is a continuation of U.S. application Ser. No. 16/044,136, filed Jul. 24, 2018, to inventors Aladar A. Szalay and Boris Minev, entitled "SMALLPDX VACCINE FOR CANCER TREATMENT," now issued as U.S. Pat. No. 10,857,225 on Dec. 8, 2020, which is a continuation of U.S. application Ser. No. 15/235,082, filed Aug. 11, 2016, to inventors Aladar A. Szalay and Boris Minev, entitled "SMALLPOX VACCINE FOR CANCER TREATMENT," now issued as U.S. Pat. No. 10,105,436 on Oct. 23, 2018, which claims the benefit of and priority to U.S. Provisional Application No. 62/317,226, filed Apr. 1, 2016, to inventors Aladar A. Szalay and Boris Minev, U.S. Provisional Application No. 62/216,292, filed Sep. 9, 2015, to inventors Aladar A. Szalay and Boris Minev, and U.S. Provisional Application No. 62/203,835, filed Aug. 11, 2015, to inventors Aladar A. Szalay and Boris Minev. The subject matter of each of the above-referenced applications is incorporated herein by reference in its entirety.

BACKGROUND OF THE INVENTION

Cancer is the second most common cause of death in the United States, exceeded only by heart disease. In the United States, cancer accounts for 1 of every 4 deaths. The 5-year relative survival rate for all cancer patients diagnosed in 1996-2003 is 66%, up from 50% in 1975-1977 (Cancer Facts & Figures American Cancer Society: Atlanta, GA (2008)). Discovering highly effective cancer treatments is a primary goal of cancer research.

SUMMARY OF THE INVENTION

Disclosed herein are methods and compositions for treating a solid tumor or hematologic malignancy in a subject.

In some embodiments, disclosed herein is a method for treating a proliferative disease (e.g., solid tumor or hematologic malignancy) in a subject, comprising administering to the subject a smallpox vaccine. In some embodiments, the smallpox vaccine is a replication competent virus. In some embodiments, the smallpox vaccine does not comprise heterologous nucleic acid. In some embodiments, the smallpox vaccine is administered by intratumoral, intravenous, intraperitoneal, intrathecal, intraventricular, intraarticular, or intraocular injection. In some embodiments, the smallpox vaccine is an attenuated New York City Board of Health (NYCBOH) strain of vaccinia virus. In some embodiments, the NYCBOH strain of vaccinia virus may be ATCC VR-118 or CJ-MVB-SPX. In some embodiments, the smallpox vaccine is selected from Dryvax, ACAM1000, ACAM2000, Lister, EM63, LIVP, Tian Tan, Copenhagen, Western Reserve, or Modified Vaccinia Ankara (MVA). In some embodiments, the solid tumor is selected from: glioblastoma, breast carcinoma, lung carcinoma, prostate carcinoma, colon carcinoma, ovarian carcinoma, neuroblastoma, central nervous system tumor, or melanoma. In some embodiments, the subject is human. In some embodiments, the subject is a pediatric patient. In some embodiments, the proliferative disease is a childhood or pediatric tumor or cancer.

In some embodiments, disclosed herein is a method for treating a solid tumor or hematologic malignancy in a subject, comprising administering to the subject a smallpox vaccine concurrently with a stem cell. In some embodiments, the stem cell is an autologous stem cell. In some embodiments, the stem cell is selected from the group consisting of adult stem cells, embryonic stem cells, fetal stem cells, mesenchymal stem cells, neural stem cells, totipotent stem cells, pluripotent stem cells, multipotent stem cells, oligopotent stem cells, unipotent stem cells, adipose stromal cells, endothelial stem cells, induced pluripotent stem cells, bone marrow stem cells, cord blood stem cells, adult peripheral blood stem cells, myoblast stem cells, small juvenile stem cells, skin fibroblast stem cells, and combinations thereof. In some embodiments, the stem cell is an adipose stromal cell.

In some embodiments, the stem cell is a modified stem cell. In some embodiments, the modified stem cell is an adult stem cell. In some embodiments, the modified stem cell is transformed with a lenti-virus or retrovirus. In some embodiments, the modified stem cell is transiently transfected with an artificial chromosome, virus or plasmid DNA. In some embodiments, the stem cell is autologous. In some embodiments, the smallpox vaccine does not comprise heterologous nucleic acid. In some embodiments, the smallpox vaccine is administered by intratumoral, intravenous, intraperitoneal, intrathecal, intraventricular, intraarticular, or intraocular injection. In some embodiments, the smallpox vaccine is an attenuated New York City Board of Health (NYCBOH) strain of vaccinia virus. In some embodiments, the NYCBOH strain of vaccinia virus may be ATCC VR-118 or CJ-MVB-SPX. In some embodiments, the smallpox vaccine is selected from Dryvax, ACAM1000, ACAM2000, Lister, EM63, LIVP, Tian Tan, Copenhagen, Western Reserve, or Modified Vaccinia Ankara (MVA). In some embodiments, the solid tumor is glioblastoma, breast carcinoma, lung carcinoma, prostate carcinoma, colon carcinoma, ovarian carcinoma, neuroblastoma, central nervous system tumor, or melanoma. In some embodiments, the stem cell and the smallpox vaccine are simultaneously administered to the subject by intratumoral, intravenous, intraperitoneal, intrathecal, intraventricular, intraarticular, or intraocular injection. In some embodiments, the stem cell and the smallpox vaccine are housed in the same vessel prior to injection into the subject. In some embodiments, the method further comprises concurrently administering a genetically engineered virus to the subject. In some embodiments, the subject is human. In some embodiments, the subject is a pediatric patient. In some embodiments, the proliferative disease is a childhood or pediatric tumor or cancer.

In some embodiments, disclosed herein is a method of treating a proliferative disease in a subject, comprising administering to the subject a smallpox vaccine concurrently with an adipose-derived stromal vascular fraction (SVF). In some embodiments, the adipose-derived SVF is autologous. In some embodiments, the adipose-derived SVF is administered to the subject within 24 hours of adipose tissue being taken from the subject. In some embodiments, the smallpox vaccine is administered by intratumoral, intravenous, intraperitoneal, intrathecal, intraventricular, intraarticular, or intraocular injection. In some embodiments, the adipose-derived SVF is removed from the subject via the Time Machine™ device. In some embodiments, the adipose-derived SVF is removed using from the subject with a 2.5 to 3 mM cannula. In some embodiments, the smallpox vaccine is an attenuated New York City Board of Health (NYCBOH) strain of vaccinia virus. In some embodiments, the NYCBOH strain of vaccinia virus may be ATCC VR-118 or CJ-MVB-SPX. In some embodiments, the smallpox vaccine is selected from Dryvax, ACAM1000, ACAM2000, Lister, EM63, LIVP, Tian Tan, Copenhagen, Western Reserve, or Modified Vaccinia Ankara (MVA). In some embodiments, the solid tumor is glioblastoma, breast carcinoma, lung carcinoma, prostate carcinoma, colon carcinoma, ovarian carcinoma, neuroblastoma, central nervous system tumor, or melanoma. In some embodiments, the subject is human. In some embodiments, the subject is a pediatric patient. In some embodiments, the proliferative disease is a childhood or pediatric tumor or cancer.

Disclosed herein, in some embodiments, is a method of treating a proliferative disease, e.g., solid tumor or a hematological malignancy, in a subject, comprising administering to the subject a smallpox vaccine concurrently with a carrier cell. In some embodiments, the carrier cell is an autologous cell from the subject. In some embodiments, the carrier cell is an immune cell selected from a granulocyte, a mast cell, a monocyte, a dendritic cell, a natural killer cell, and a lymphocyte. In some embodiments, the immune cell is a lymphocyte. In some embodiments, the lymphocyte is a T cell. In some embodiments, the carrier cell comprises heterologous nucleic acid. In some embodiments, the smallpox vaccine and the carrier cell are cultured together in vitro prior to administration to the subject. In some embodiments, smallpox vaccine and the carrier cell are housed in the same vessel prior to administration into the subject. In some embodiments, the subject is human. In some embodiments, the subject is a pediatric patient. In some embodiments, the proliferative disease is a childhood or pediatric tumor or cancer.

Disclosed herein, in some embodiments, is a composition comprising: (a) smallpox vaccine and (b) a stem cell. In some embodiments, the composition further includes a pharmaceutically acceptable carrier. In some embodiments, the stem cell is selected from is selected from the group consisting of adult stem cells, embryonic stem cells, fetal stem cells, mesenchymal stem cells, neural stem cells, totipotent stem cells, pluripotent stem cells, multipotent stem cells, oligopotent stem cells, unipotent stem cells, adipose stromal cells, endothelial stem cells, induced pluripotent stem cells, bone marrow stem cells, cord blood stem cells, adult peripheral blood stem cells, myoblast stem cells, small juvenile stem cells, skin fibroblast stem cells, and combinations thereof. In some embodiments, the stem cell is an adipose stromal cell. In some embodiments, the stem cell is a modified stem cell. In some embodiments, the modified stem cell is an adult stem cell. In some embodiments, the modified stem cell is transformed with a lentivirus or retrovirus. In some embodiments, the modified stem cell is transiently transfected with an artificial chromosome, virus or plasmid DNA. In some embodiments, the smallpox vaccine does not comprise heterologous nucleic acid. In some embodiments, the composition further comprises a genetically engineered virus.

Disclosed herein, in some embodiments, is a composition comprising: (a) smallpox vaccine; and (b) an immune cell, such as a granulocyte, a mast cell, a monocyte, a dendritic cell, a natural killer cell, or a lymphocyte. In some embodiments, the composition further includes a pharmaceutically acceptable carrier. In some embodiments, the immune cell is a lymphocyte. In some embodiments, the lymphocyte is a T cell. In some embodiments, the immune cell comprises heterologous nucleic acid.

Disclosed herein, in some embodiments, is a composition comprising: (a) smallpox vaccine; and (b) isolated adipose stromal vascular fraction (SVF).

Further disclosed herein, in some embodiments, is a host cell, or a tumor cell, or a mammalian organism comprising a composition of any of the compositions including smallpox vaccine and a stem cell; or including smallpox vaccine and an immune cell selected from a granulocyte, a mast cell, a monocyte, a dendritic cell, a natural killer cell, and a lymphocyte; or including smallpox vaccine and an isolated adipose stromal vascular fraction (SVF).

BRIEF DESCRIPTION OF DRAWINGS

FIGS. 1A and 1B show the oncolysis effect on a panel of human tumor cell lines after infection with Lister and ACAM2000 virus strains, respectively.

DETAILED DESCRIPTION

In spite of great advances in anticancer treatments over the past 30 years, cancer remains the leading cause of death around the world. Provided herein are methods and compositions for treating a tumor, cancer or metastasis in a subject, such as a human subject or an animal subject. Specifically, disclosed herein are methods and compositions for activating the body's own immune system to fight cancer by administration of a smallpox vaccine.

Definitions

As used herein, a subject includes any animal for which diagnosis, screening, monitoring or treatment is contemplated. Animals include mammals such as primates and domesticated animals. Preferably, the primate is human. A patient refers to a subject such as a mammal, primate, human, or livestock subject afflicted with a disease condition or for which a disease condition is to be determined or risk of a disease condition is to be determined.

As used herein, a "pediatric patient" refers to persons who are age 21 years or younger at the time of their diagnosis or treatment. In some embodiments, a pediatric patient can be selected from a neonate, an infant, a child, and an adolescent. A "neonate" refers to persons from birth through the first 38 days of life. An "infant" refers to persons 29 days of age to less than two years of age. A "child" refers to persons two years of age to less than 12 years of age. An "adolescent" refers to persons 12 years of age through 21 years of age (up to, but not including, the twenty-second birthday). In some embodiments, a pediatric patient is greater than 12 months in age. In some embodiments, a pediatric patient is less than 18 years in age.

As used herein, the term "concurrently" as referring to administration of a smallpox vaccine and a cell, refers to administration within 48 hours of each other. In some embodiments, the smallpox vaccine and cell are administered within 36 hours of each other, within 24 hours of each other, within 12 hours of each other, within 10 hours of each other, within 8 hours of each other, within 6 hours of each other, within 4 hours of each other, within two hours of each other, within 1 hour of each other.

The term "autologous," "autologous cell" or "autologous transplantation" as used herein in relation to cell transplantation indicates that the donor and recipient of the cells is the same individual. The term "allogenic," "allogenic cell" or "allogenic transplantation" as used herein in relation to cell transplantation indicates that the donor and recipient of the cells are different individuals of the same species.

The term "adipose tissue" as used herein refers to body fat tissue, which is a loose connective tissue composed mostly of adipocytes. In addition to adipocytes, adipose tissue contains the stromal vascular fraction (SVF) of cells including preadipocytes, fibroblasts, vascular endothelial cells, a variety of immune cells, as well as regenerative stem cells.

The term "adipose stem cell" or "adipose-derived adult stem cell (ADASC)" as used herein refers to stem cells isolatable from adipose tissues, which are pluripotent stem cells capable of differentiation into numerous cell types. Adipose stem cells are found to be equivalent, if not superior to, bone marrow stem cells in terms of cell differentiation potential, angiogenesis and anti-inflammatory effects.

The term "tumor" or "tumor cell," as used herein, refers to any type of tumor, including solid tumors or non-solid tumors, dispersed tumors, metastatic or disseminated tumors, or tumor cells from any form of tumor.

The term "vaccine" as used herein, refers to any type of biological preparation contributing to or soliciting active immune responses against a particular disease or pathogen. Such biological preparation can include, but is not limited to, an antigen derived from a disease-causing agent or a portion of an antigen derived from a disease-causing agent. Such biological preparation can also be in the form of live attenuated preparation, including live, or weakened or modified disease causing agents or pathogens; or in the form of inactivated or killed disease-causing agents or pathogens. Alternative forms of such biological preparation further include, but are not limited to, the forms of subunit, toxoid, conjugate, DNA and recombinant vectors, or any suitable forms that might become developed or available in the future for soliciting active immune responses thereagainst.

It should be noted that in some embodiments, while the term "vaccine" is used herein, the vaccine need not provide significant immunity against smallpox (or any other pathogen), so long as it is effective against a cancer or proliferative disease as described herein. For example, the vaccine may be any immunogenic or infectious composition that treats the cancer. In some cases, the term is used to identify certain materials or compositions, and not necessarily the ability of material or composition to provide immunity against smallpox, for example. In some embodiments the composition or material that is administered can be a virus that elicits an immunogenic response against a tumor cell, and or one that elicits an immunogenic response against smallpox. The virus can be from any strain of virus, including for example, one or more listed below and elsewhere herein, including those that are not part of approved or contemplated vaccines.

As used herein, "virus" refers to any of a large group of entities referred to as viruses. Viruses typically contain a protein coat surrounding an RNA or DNA core of genetic material, but no semipermeable membrane, and are capable of growth and multiplication only in living cells. Viruses for use in the methods provided herein include, but are not limited, to a poxvirus, adenovirus, herpes simplex virus, Newcastle disease virus, vesicular stomatitis virus, mumps virus, influenza virus, measles virus, reovirus, human immunodeficiency virus (HIV), hanta virus, myxoma virus, cytomegalovirus (CMV), lentivirus, and any plant or insect virus.

As used herein, "hematologic malignancy" refers to tumors of the blood and lymphatic system (e.g. Hodgkin's disease, Non-Hodgkin's lymphoma, Burkitt's lymphoma, AIDS-related lymphomas, malignant immunoproliferative diseases, multiple myeloma and malignant plasma cell neoplasms, lymphoid leukemia, myeloid leukemia, acute or chronic lymphocytic leukemia, monocytic leukemia, other leukemias of specified cell type, leukemia of unspecified cell type, other and unspecified malignant neoplasms of lymphoid, hematopoietic and related tissues, for example diffuse large cell lymphoma, T-cell lymphoma or cutaneous T-cell lymphoma).

As used herein, "heterologous nucleic acid" refers to a nucleic acid, DNA or RNA, which has been introduced into a virus or a cell (or the cell's ancestor). Such heterologous nucleic acid may comprise the sequence and operable regulatory elements for genes. For example, the heterologous nucleic acid may comprise a selection marker gene, a suicide gene, or a gene expressing a useful protein product that is not expressed endogenously, or expressed endogenously at low levels.

Smallpox Vaccines and Anti-Cancer Compositions

Disclosed herein, in some embodiments, is a method for treating a solid tumor or hematologic malignancy in a subject, comprising administering to the subject a smallpox vaccine, other smallpox immunogenic composition, or other composition (immunogenic or otherwise) that is capable of eliciting a similar response. Although the terms smallpox vaccines may be used throughout, it should be understood that other compositions that may not formally be approved or designated "vaccines" compositions can be used instead. For example, other smallpox immunogenic compositions or other immunogenic compositions can be used. In some embodiments, the smallpox vaccine does not comprise heterologous nucleic acid. In some embodiments, the smallpox vaccine is administered by intratumoral, intravenous, intraperitoneal, intrathecal, intraventricular, intraarticular, or intraocular injection, or intradermal injection, or any suitable methods delivering thereof.

Variola virus is the cause of smallpox. In contrast to variola virus, vaccinia virus, which has been used for smallpox vaccination, does not normally cause systemic disease in immune-competent individuals and it has therefore been used as a live vaccine to immunize against smallpox. Successful worldwide vaccination with Vaccinia virus culminated in the eradication of smallpox as a natural disease in the 1980s. Since then, vaccination has been discontinued for many years, except for people at higher risk of poxvirus infections (e.g., laboratory workers). Although the United States discontinued routine childhood immunization against smallpox in 1972, the use of smallpox vaccine is generally considered safe for pediatric use.

In some embodiments, an attenuated strain derived from a pathogenic virus is used for the manufacturing of a live vaccine. Non-limiting examples of viral strains that have been used as a smallpox vaccine include but are not limited to the Lister (also known as Elstree), New York City Board of Health ("NYCBH strain"), Dairen, Ikeda, LC16M8, Western Reserve (WR), Copenhagen, Tashkent, Tian Tan, Wyeth, IHD-J, and IHD-W, Brighton, Ankara, MVA, Dairen I, LIPV, LC16MO, LIVP, WR 65-16, EM63, and Connaught strains. In some embodiments, the smallpox vaccine utilized in the methods disclosed herein is an attenuated New York City Board of Health (NYCBOH) strain of vaccinia virus. In some embodiments, the NYCBOH strain of vaccinia virus may be ATCC VR-118 or CJ-MVB-SPX.

In some embodiments, the smallpox vaccine is non-attenuated.

In some embodiments, the smallpox vaccine is selected from Dryvax, ACAM1000, ACAM2000, Lister, EM63, LIVP, Tian Tan, Copenhagen, Western Reserve, or Modified Vaccinia Ankara (MVA). In some embodiments, the smallpox vaccine is not deficient in any genes present in one or more of these strains.

In some embodiments, the smallpox vaccine is a replication competent virus. In some embodiments, the smallpox vaccine is replication deficient.

The methods disclosed herein can be used to treat any solid tumor or hematologic malignancy. Tumors that can be treated by the methods disclosed herein include, but are not limited to a bladder tumor, breast tumor, prostate tumor, carcinoma, basal cell carcinoma, biliary tract cancer, bladder cancer, bone cancer, brain cancer, CNS cancer, glioma tumor, cervical cancer, choriocarcinoma, colon and rectum cancer, connective tissue cancer, cancer of the digestive system, endometrial cancer, esophageal cancer, eye cancer, cancer of the head and neck, gastric cancer, intra-epithelial neoplasm, kidney cancer, larynx cancer, leukemia, liver cancer, lung cancer, lymphoma, Hodgkin's lymphoma, Non-Hodgkin's lymphoma, melanoma, myeloma, neuroblastoma, oral cavity cancer, ovarian cancer, pancreatic cancer, retinoblastoma, rhabdomyosarcoma, rectal cancer, renal cancer, cancer of the respiratory system, sarcoma, skin cancer, stomach cancer, testicular cancer, thyroid cancer, uterine cancer, and cancer of the urinary system, such as lymphosarcoma, osteosarcoma, mammary tumors, mastocytoma, brain tumor, melanoma, adenosquamous carcinoma, carcinoid lung tumor, bronchial gland tumor, bronchiolar adenocarcinoma, small cell lung cancer, non-small cell lung cancers, fibroma, myxochondroma, pulmonary sarcoma, neurosarcoma, osteoma, papilloma, retinoblastoma, Ewing's sarcoma, Wilms' tumor, Burkitt's lymphoma, microglioma, neuroblastoma, osteoclastoma, oral neoplasia, fibrosarcoma, osteosarcoma and rhabdomyosarcoma, genital squamous cell carcinoma, transmissible venereal tumor, testicular tumor, seminoma, Sertoli cell tumor, hemangiopericytoma, histiocytoma, chloroma, granulocytic sarcoma, corneal papilloma, corneal squamous cell carcinoma, hemangiosarcoma, pleural mesothelioma, basal cell tumor, thymoma, stomach tumor, adrenal gland carcinoma, oral papillomatosis, hemangioendothelioma, cystadenoma, follicular lymphoma, intestinal lymphosarcoma, fibrosarcoma, and pulmonary squamous cell carcinoma, leukemia, hemangiopericytoma, ocular neoplasia, preputial fibrosarcoma, ulcerative squamous cell carcinoma, preputial carcinoma, connective tissue neoplasia, mastocytoma, hepatocellular carcinoma, lymphoma, pulmonary adenomatosis, pulmonary sarcoma, Rous sarcoma, reticulo-endotheliosis, fibrosarcoma, nephroblastoma, B-cell lymphoma, lymphoid leukosis, retinoblastoma, hepatic neoplasia, lymphosarcoma, plasmacytoid leukemia, swim bladder sarcoma (in fish), caseous lumphadenitis, lung carcinoma, insulinoma, lymphoma, sarcoma, salivary gland tumors, neuroma, pancreatic islet cell tumor, gastric MALT lymphoma and gastric adenocarcinoma.

In some embodiments, the tumor is selected from metastatic melanoma; esophageal and gastric adenocarcinoma; cholangiocarcinoma (any stage); pancreatic adenocarcinoma (any stage); gallbladder cancer (any stage); high-grade mucinous appendix cancer (any stage); high-grade gastrointestinal neuroendocrine cancer (any stage); mesothelioma (any stage); soft tissue sarcoma; prostate cancer; renal cell carcinoma; lung small cell carcinoma; lung non-small cell carcinoma; head and neck squamous cell carcinoma; colorectal cancer; ovarian carcinoma; hepatocellular carcinoma; and glioblastoma.

In some embodiments, the tumor is selected from: glioblastoma, breast carcinoma, lung carcinoma, prostate carcinoma, colon carcinoma, ovarian carcinoma, neuroblastoma, central nervous system tumor, and melanoma.

In some embodiments, the tumor or cancer that can be treated is a childhood or pediatric tumor or cancer. For example, the tumor or cancer can be a leukemia, a lymphoma, a sarcoma, and the like. Non-limiting examples of leukemia include acute lymphoblastic leukemia (ALL) and acute myeloid leukemia (AML). Non-limiting examples of types of lymphomas include Hodgkin disease (or Hodgkin lymphoma) and non-Hodgkin lymphoma (e.g., B and T cell lymphomas). Non-limiting examples of solid tumors or cancers for pediatric patients include brain tumors, Ewing Sarcoma, eye cancer (retinoblastoma), germ cell tumors, Kidney tumors (e.g., Wilms Tumor), liver cancer, neuroblastoma, osteosarcoma, rhabdomyosarcoma, skin cancer (e.g., melanoma), soft tissue sarcoma and thyroid cancer. In some embodiments, the subject is human. In some embodiments, the subject is a pediatric patient. In some embodiments, the subject is a neonate. In some embodiments, the subject is an infant. In some embodiments, the subject is a child. In some embodiments, the subject is an adolescent. In some embodiments, the subject is greater than 12 months in age. In some embodiments the subject is less than 18 years in age.

Smallpox Vaccine and Composition Carriers

Immunogenic cell death inducers, like viruses, are subject to significant elimination and/or neutralization following systemic application. Therefore, in some embodiments, disclosed herein are suitable vehicles for shielding the disclosed smallpox vaccines from the elements of the humoral and cellular immunity in the blood stream, as well as methods for their targeted delivery to tumor sites.

Thus, in some embodiments, disclosed herein is a method of treating a solid tumor or a hematological malignancy in a subject, comprising administering to the subject a smallpox vaccine concurrently with a carrier cell. In some embodiments, the carrier cell is an autologous cell from the subject. In other embodiments the cell can be non-autologous or allogeneic.

In some embodiments, the carrier cell is an insect cell, a reptile cell, an amphibian cell, an avian cell or a mammalian cell. In some embodiments, the carrier cell is an immortalized cell. In some embodiments, the carrier cell is a neoplastic cell derived from a tumor. In some embodiments, the carrier is a human cell.

In some embodiments, the smallpox vaccine, or other composition as described herein, and the carrier cell are administered simultaneously. In some embodiments, the smallpox vaccine and the carrier cell are administered simultaneously through one administration vehicle. In some embodiments, the smallpox vaccine and the carrier cell are administered simultaneously through one vessel, e.g. a syringe, via intratumoral, intravenous, intraperitoneal, intrathecal, intraventricular, intraarticular, or intraocular injection or intradermal injection, or any suitable methods delivering thereof.

Stem Cells

Recent studies have demonstrated extensive homing of stem cells to glioma tumors and the potential of gene loading into stem cells using viral vectors. These studies indicate that the stem cells are a promising candidate as a vehicle for delivery of the anti-cancer agent to the tumor sites.

Accordingly, disclosed herein, in some embodiments, is the use of stem cells as a vehicle for in vivo delivery of smallpox vaccine to the cancer cells or tumor. In some embodiments, the smallpox vaccine is mixed with the vehicle stem cells to avoid the immune system from clearing the virus before the virus reaches the tumor. Thus, in some embodiments, disclosed herein is a method for treating a solid tumor or hematologic malignancy in a subject, comprising administering to the subject a smallpox vaccine concurrently with a stem cell. In some embodiments, the smallpox vaccine does not comprise heterologous nucleic acid. In some embodiments, the method further comprises concurrently administering a genetically engineered virus to the subject. Some embodiments relate to methods of preparing the preparing the stem cell and smallpox vaccine compositions prior to administration.

In some embodiments, the vehicle stem cell is an autologous stem cell. In others it is non-autologous or allogeneic.

In some embodiments, the vehicle stem cells are selected from the group consisting of adult stem cells, embryonic stem cells, fetal stem cells, mesenchymal stem cells, neural stem cells, totipotent stem cells, pluripotent stem cells, multipotent stem cells, oligopotent stem cells, unipotent stem cells, adipose stromal cells, endothelial stem cells, induced pluripotent stem cells, bone marrow stem cells, cord blood stem cells, adult peripheral blood stem cells, myoblast stem cells, small juvenile stem cells, skin fibroblast stem cells, and combinations thereof. In some embodiments, the modified stem cell is an umbilical cord-derived mesenchymal like cell. In some embodiments, the umbilical cord-derived mesenchymal-like cell is an ImmStem™ cell. In some embodiments, the stem cell is an adipose stromal cell. One or more of the above-listed cells can be specifically excluded from some embodied compositions and methods.

In some embodiments, the vehicle stem cells are modified. Particularly, in some embodiments, the modified stem cell is an adult stem cell (ASC). In some embodiments, the modified stem cell is transformed with a viral vector. In some embodiments, the modified stem cell is transformed with a lenti-virus or retrovirus. In some embodiments, the modified stem cell is transformed with the recombinant virus. In some embodiments, the modified stem cell is transiently transfected with an artificial chromosome, virus or plasmid DNA. In some embodiments, the virus is an oncolytic virus. In some embodiments, the virus is a vaccinia virus. In some embodiments, the virus is a replication-competent oncolytic vaccinia virus (VACV). In some embodiments, the modified stem cell is capable of localizing to the tumor. In some embodiments, the modified stem cell is autologous. In some embodiments, the modified stem cell is allogeneic.

In some embodiments, the modified stem cell is an adult stem cell. In some embodiments, the modified stem cell is transformed with a lenti-virus or retrovirus. In some embodiments, the modified stem cell is transiently transfected with an artificial chromosome, virus or plasmid DNA. In some embodiments, the modified stem cell is capable of localizing to the tumor. In some embodiments, the modified stem cell is autologous. In some embodiments, the modified stem cell is allogeneic. In some embodiments, the modified stem cell is selected from the group consisting of adult stem cells, embryonic stem cells, fetal stem cells, mesenchymal stem cells, neural stem cells, totipotent stem cells, pluripotent stem cells, multipotent stem cells, oligopotent stem cells, unipotent stem cells, adipose stromal cells, endothelial stem cells, and combinations thereof. In some embodiments, the modified stem cell is an umbilical cord-derived mesenchymal like cell. In some embodiments, the umbilical cord-derived mesenchymal-like cell is an ImmStem™ cell.

ImmStem are umbilical cord-derived mesenchymal-like cells, which possess pluripotent differentiation capacity and are characterized by unique surface markers and growth factor production. ImmStem possess numerous advantages compared to other stem cell sources, including ease of collection, higher rate of proliferation, very low immunogenicity, and ability to differentiate into tissues representative of all three germ layer components. In comparison to other mesenchymal stem cell (MSC) subtypes, ImmStem has demonstrated upregulated anti-inflammatory and migratory capacity due to a "cytokine priming" step, which is performed prior to administration. ImmStem cells are generated from human umbilical cords, which are obtained from full term women immediately after delivery. To stimulate a stress response, the cells are cultured for about 48 hours with interferon gamma. In some embodiments the culturing with IFN-gamma can be from 1 to 72 hours or any value or sub range therein.

In some embodiments, the smallpox vaccine and/or the stem cell are administered to a subject by any suitable method of administration. In some embodiments, the smallpox vaccine and/or the stem cell are administered by intratumoral, intravenous, intraperitoneal, intrathecal, intraventricular, intraarticular, or intraocular injection.

In some embodiments, the smallpox vaccine and the stem cell are administered simultaneously. In some embodiments, the smallpox vaccine and the stem cell are administered simultaneously through one administration vehicle. In some embodiments, the smallpox vaccine and the stem cell are administered simultaneously through one vessel, e.g., a syringe, via intratumoral, intravenous, intraperitoneal, intrathecal, intraventricular, intraarticular, or intraocular injection or intradermal injection, or any suitable methods delivering thereof.

In some embodiments, the tumor is selected from metastatic melanoma; esophageal and gastric adenocarcinoma; cholangiocarcinoma (any stage); pancreatic adenocarcinoma (any stage); gallbladder cancer (any stage); high-grade mucinous appendix cancer (any stage); high-grade gastrointestinal neuroendocrine cancer (any stage); mesothelioma (any stage); soft tissue sarcoma; prostate cancer; renal cell carcinoma; lung small cell carcinoma; lung non-small cell carcinoma; head and neck squamous cell carcinoma; colorectal cancer; ovarian carcinoma; hepatocellular carcinoma; and glioblastoma.

In some embodiments, the tumor is selected from: glioblastoma, breast carcinoma, lung carcinoma, prostate carcinoma, colon carcinoma, ovarian carcinoma, neuroblastoma, central nervous system tumor, and melanoma. In some embodiments, one or more of the listed tumor, cancer or malignancies can be specifically excluded from the herein described compositions and/or methods.

Immune Cells

Further disclosed herein, in some embodiments, is the use of immune cells as a vehicle for in vivo delivery of smallpox vaccine to the cancer cells or tumor. In some embodiments, the anticancer agent is mixed with the vehicle immune carrier cells to avoid the immune system from clearing the virus before the virus reaches the tumor. Thus, in some embodiments, disclosed herein is a method of treating a solid tumor or a hematological malignancy in a subject, comprising administering to the subject a smallpox vaccine concurrently with an immune cell selected from a granulocyte, a mast cell, a monocyte, a dendritic cell, a natural killer cell, and a lymphocyte. In some embodiments, the immune cell is an autologous cell. In some embodiments, the immune cell is a lymphocyte. In some embodiments, the lymphocyte is a T cell. In some embodiments, the immune cell comprises heterologous nucleic acid. In some embodiments, the smallpox vaccine and immune cell are cultured together in vitro together prior to administration to the subject.

In some embodiments, the smallpox vaccine and the immune cell are administered simultaneously. In some embodiments, the smallpox vaccine and the immune cell are administered simultaneously through one administration vehicle. In some embodiments, the smallpox vaccine and the immune cell are administered simultaneously through one vessel, e.g. a syringe, via intratumoral, intravenous, intraperitoneal, intrathecal, intraventricular, intraarticular, or intraocular injection or intradermal injection, or any suitable methods delivering thereof.

In some embodiments, the tumor is selected from metastatic melanoma; esophageal and gastric adenocarcinoma; cholangiocarcinoma (any stage); pancreatic adenocarcinoma (any stage); gallbladder cancer (any stage); high-grade mucinous appendix cancer (any stage); high-grade gastrointestinal neuroendocrine cancer (any stage); mesothelioma (any stage); soft tissue sarcoma; prostate cancer; renal cell carcinoma; lung small cell carcinoma; lung non-small cell carcinoma; head and neck squamous cell carcinoma; colorectal cancer; ovarian carcinoma; hepatocellular carcinoma; and glioblastoma. In some embodiments, one or more of the listed tumor, cancer or malignancies can be specifically excluded from the herein described compositions and/or methods.

In some embodiments, the tumor is selected from: glioblastoma, breast carcinoma, lung carcinoma, prostate carcinoma, colon carcinoma, ovarian carcinoma, neuroblastoma, central nervous system tumor, and melanoma.

Adipose Stromal Vascular Fraction

Disclosed herein, in some embodiments, is a method of treating a proliferative disease in a subject, comprising administering to the subject a smallpox vaccine concurrently with an adipose-derived stromal vascular fraction (SVF), wherein the adipose-derived SVF is autologous. In some embodiments, the adipose-derived SVF is administered to the subject within about 24 hours of adipose tissue being taken from the subject. In some embodiments the adipose-derived SVF can be administered at any time after collection and up to about 48 hours post collection, or any time point or time sub range there between. In some embodiments, the smallpox vaccine is administered by intratumoral, intravenous, intraperitoneal, intrathecal, intraventricular, intraarticular, or intraocular injection or intradermal injection, or any suitable methods delivering thereof.

Adipose tissue is an alternative to bone marrow as a source of stem cells for the following reasons: a) extraction of adipose derived cells is a simpler, less invasive procedure than bone marrow extraction; b) adipose tissue contains a higher content of mesenchymal stem cells (MSC) as compared to bone marrow; c) MSC from adipose tissue do not decrease in number with aging and can therefore serve as an autologous cell source for all patients; and d) adipose tissue is also a source of unique cell populations in addition to MSC that have therapeutic potential, including endothelial cells and regulatory T cells.

MSC are poorly immunogenic and possess immune modulatory activity, features that are conserved among MSC from various tissues. This weak immunogenicity is believed to permit the survival and activity of allogeneic MSC when administered therapeutically.

In addition to its stem/progenitor cell content, the adipose-derived SVF is known to contain, inter alia, monocytes/macrophages and endothelial cells.

SVF derived from whole lipoaspirate alleviates the need for extensive processing of the cells within, thereby minimizing the number of steps where contamination could be introduced (Kurita et al., Plast Reconstr Surg 2008, 121: 1033-1041; discussion 1042-1033; Yoshimura et al., Aesthetic Plast Surg 2008, 32:48-55; discussion 56-47). The safety of administration of adipose-derived cells is supported by autologous fat grafting, a common practice in cosmetic surgery (Hang-Fu et al., Aesthetic Plast Surg 1995, 19:427-437). Each of the aforementioned references is incorporated herein by reference in its entirety.

In some embodiments, the adipose-derived SVF is obtained by means and knowledge known to one of skill in the art. In some embodiments, the adipose-derived SVF is removed from the subject via the Time Machine™ device. In some embodiment, the adipose-derived SVF is removed from the subject with a 2.5 to 3 mM cannula. In some embodiments one or more of the following devices can be utilized, PNC's Multi Station, CHA Biotech Cha-Station, Cytori Celution® 800/CRS System, and Medi-Khan's Lipokit with MaxStem.

In some embodiments, the smallpox vaccine and the adipose-derived SVF are administered concurrently. In some embodiments, the smallpox vaccine and the adipose-derived SVF are administered simultaneously. In some embodiments, the smallpox vaccine and the adipose-derived SVF are administered simultaneously through one administration vehicle. In some embodiments, the smallpox vaccine and the adipose-derived SVF are administered simultaneously through one vessel, e.g. a syringe, via intratumoral, intravenous, intraperitoneal, intrathecal, intraventricular, intraarticular, or intraocular injection or intradermal injection, or any suitable methods delivering thereof.

In some embodiments, the tumor is selected from metastatic melanoma; esophageal and gastric adenocarcinoma; cholangiocarcinoma (any stage); pancreatic adenocarcinoma (any stage); gallbladder cancer (any stage); high-grade mucinous appendix cancer (any stage); high-grade gastrointestinal neuroendocrine cancer (any stage); mesothelioma (any stage); soft tissue sarcoma; prostate cancer; renal cell carcinoma; lung small cell carcinoma; lung non-small cell carcinoma; head and neck squamous cell carcinoma; colorectal cancer; ovarian carcinoma; hepatocellular carcinoma; and glioblastoma. One or more of the above-mentioned tumors can be specifically excluded from the compositions and methods of some embodiments.

In some embodiments, the tumor is selected from: glioblastoma, breast carcinoma, lung carcinoma, prostate carcinoma, colon carcinoma, ovarian carcinoma, neuroblastoma, central nervous system tumor, and melanoma. One or more of the above-mentioned tumors can be specifically excluded from the compositions and methods of some embodiments.

Compositions

Disclosed herein are various compositions useful in the methods disclosed herein of treating a solid tumor or hematological malignancy.

In some embodiments, disclosed herein is a composition comprising a smallpox vaccine and a carrier cell, as disclosed herein.

In some embodiments, disclosed herein is a composition comprising: (a) smallpox vaccine; and (b) a stem cell. In some embodiments, the stem cell is selected from the group consisting of adult stem cells, embryonic stem cells, fetal stem cells, mesenchymal stem cells, neural stem cells, totipotent stem cells, pluripotent stem cells, multipotent stem cells, oligopotent stem cells, unipotent stem cells, adipose stromal cells, endothelial stem cells, and combinations thereof. In some embodiments, the stem cell is an adipose stromal cell. In some embodiments, the stem cell is a modified stem cell. In some embodiments, the modified stem cell is an adult stem cell. In some embodiments, the modified stem cell is transformed with a lenti-virus or retrovirus. In some embodiments, wherein the modified stem cell is transiently transfected with an artificial chromosome, virus or plasmid DNA. In some embodiments, the smallpox vaccine does not comprise heterologous nucleic acid. In some embodiments, the composition further comprises a genetically engineered virus. One or more of the above-mentioned components can be specifically excluded from the compositions and methods of some embodiments.

In some embodiments, disclosed herein is a composition comprising: (a) smallpox vaccine; and (b) an immune cell selected from a granulocyte, a mast cell, a monocyte, a dendritic cell, a natural killer cell, and a lymphocyte. In some embodiments, the immune cell is a lymphocyte.

In some embodiments, the lymphocyte is a T cell. In some embodiments, the immune cell comprises heterologous nucleic acid.

In some embodiments, disclosed herein is a composition comprising: (a) smallpox vaccine; and (b) isolated adipose stromal vascular fraction (SVF).

In some embodiments, the compositions disclosed herein comprise a pharmaceutically acceptable carrier. As used herein, the term "pharmaceutically acceptable carrier" refers to solvents, diluents, preservatives, dispersion or suspension aids, isotonic agents, thickening or emulsifying agents, solid binders, and lubricants, appropriate for the particular dosage form. The skilled artisan is aware of a variety of different carriers that may be used in formulating pharmaceutical compositions and knows techniques for the preparation thereof (See Remington's Pharmaceutical Sciences Ed. by Gennaro, Mack Publishing, Easton, Pa., 1995; which is incorporated herein in its entirety by reference). The pharmaceutically acceptable carriers may include, but are not limited to Ringer's solution, isotonic saline, starches, potato starch, sugars, glucose, powdered tragacanth, malt, gelatin, talc, cellulose and its derivatives, ethyl cellulose, sodium carboxymethyl cellulose, cellulose acetate excipients, cocoa butter, suppository waxes, agar, alginic acid, oils, cottonseed oil, peanut oil, safflower oil, sesame oil, olive oil, soybean oil, corn oil, glycols, propylene glycol, esters, ethyl laurate, ethyl oleate, buffering agents, aluminum hydroxide, magnesium hydroxide, phosphate buffer solutions, pyrogen-free water, ethyl alcohol, other non-toxic compatible lubricants, sodium lauryl sulfate, magnesium stearate, coloring agents, releasing agents, coating agents, sweetening, flavoring and perfuming agents. Pharmaceutically acceptable carriers may also include preservatives and antioxidants. One or more of the above-mentioned materials can be specifically excluded from the compositions and methods of some embodiments.

A composition disclosed herein comprising a live smallpox vaccine may comprise an adjuvant. Optionally, one or more compounds having adjuvant activity may be included in the vaccine. Adjuvants are non-specific stimulators of the immune system. They enhance the immune response of the host to the vaccine. Examples of adjuvants known in the art are Freund's Complete and Incomplete adjuvant, vitamin E, non-ionic block polymers, muramyldipeptides, ISCOMs (immune stimulating complexes), saponins, mineral oil, vegetable oil, and Carbopol. Adjuvants, especially suitable for mucosal application are, for example, *E. coli* heat-labile toxin (LT) or Cholera toxin (CT). Other suitable adjuvants are for example aluminium hydroxide, aluminium phosphate or aluminium oxide, oil-emulsions (e.g., of Bayol F® or Marcol 52®, saponins or vitamin-E solubilisate). One or more of the above-mentioned materials can be specifically excluded from the compositions and methods of some embodiments.

Administration of Treatment Modalities

The effective dosage of each of the treatment modalities disclosed herein may vary depending on various factors, including but not limited to the particular treatment, compound or pharmaceutical composition employed, the mode of administration, the condition being treated, and/or the severity of the condition being treated. Thus, the dosage regimen of the combination of the invention is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites.

Methods of preparing pharmaceutical compositions comprising the relevant treatments disclosed herein are known in the art and will be apparent from the art, from known standard references, such as Remington's Pharmaceutical Sciences, Mack Publishing Company, Easton, Pa., 18th edition (1990), which is incorporated herein by reference in its entirety.

In some embodiments, the smallpox vaccine and/or cells disclosed herein are administered to a subject by any appropriate method. In some embodiments, the smallpox vaccine and/or cells disclosed herein are administered by intratumoral, intravenous, intraperitoneal, intrathecal, intraventricular, intraarticular, intraocular, or intradermal injection, or any suitable methods delivering thereof.

The amount of vaccine administered to an average-sized adult can be, for example, $1\times10^{2}$ to $1\times10^{10}$ plaque-forming units, $1\times10^{3}$ to $1\times10^{8}$ plaque-forming units $1\times10^{4}$ to $1\times10^{6}$ plaque-forming units, or any value or sub range there between. As a specific example, about $2.5\times10^{5}$ plaque-forming units can be used.

It should be understood that the embodiments described herein are not limited to vaccinations or vaccinating per se, but also relate to generating an immune response or reaction to cancer cells. While the words "vaccine," "vaccination," or other like terms are used for convenience, it should be understood that such embodiments also relate to immune compositions, immunogenic compositions, immune response generation, immunization, etc., where absolute prophylactic immunity is not required or generated. For example, the embodiments referring to vaccination also can relate to generating or to assisting in creating an immunogenic or immune response against a tumor cell or tumor, regardless of whether that response results in absolute eradication or immunization against such tumor cell, tumor or the cancer.

The disclosures illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

Other embodiments are set forth within the claims.

EXAMPLES

Example 1: Preparation of ACAM2000 Vaccine

The vaccine vial should be removed from cold storage and brought to room temperature before reconstitution. The flip cap seals of the vaccine and diluent vials are removed, and each rubber stopper is wiped with an isopropyl alcohol swab and allowed to dry thoroughly.

Using aseptic technique and a sterile 1 mL syringe fitted with a 25 gauge×⅝" needle (provided), draw up 0.3 mL of diluent and transfer the entire content of the syringe to the vaccine vial. Gently swirl to mix but try not to get product on the rubber stopper. The reconstituted vaccine should be a clear to slightly hazy, colorless to straw-colored liquid free from extraneous matter. Reconstituted vaccine should be inspected visually for particulate matter and discoloration prior to administration. If particulate matter or discoloration is observed, the vaccine should not be used and the vial should be disposed safely.

After reconstitution of the lyophilized preparation, each vial contains approximately $2.5\text{-}12.5\times10^7$ plaque-forming units (pfu) of vaccinia virus (live). After reconstitution, ACAM2000 vaccine may be used within 6 to 8 hours if kept at room temperature (20-25° C., 68-77° F.). Unused, reconstituted ACAM2000 vaccine may be stored in a refrigerator (2-8° C., 36-46° F.) up to 30 days, after which it should be discarded as a biohazardous material.

Personnel preparing and administering the vaccine should wear surgical or protective gloves and avoid contact of vaccine with skin, eyes or mucous membranes.

The vaccine vial, its stopper, the diluent syringe, the vented needle used for reconstitution, the needle used for administration, and any material that came in contact with the vaccine should be discarded in leak-proof, puncture-proof biohazard containers. These containers should then be disposed of appropriately.

For vaccine application, gently swirl the vaccine vial to mix but try not to get product on the rubber stopper.

Using aseptic technique and a sterile 1 mL syringe fitted with a 25 gauge×⅝" needle, draw up the entire content of the vial and transfer it to the labeled 20 cc syringe containing the SVF fraction.

Gently swirl to mix well and incubate the syringe at 37° C. for 2 to 4 hours.

Example 2: Retrieval and Preparation of Adipose Stromal Vascular Fraction

Patient will receive local anesthesia consisting of lidocaine 0.5% with epinephrine 1:400,000 with HCO3 8.4% titrated to pH of 7.4 (generally 5 cc of HCO3 in total volume of 60 cc) and undergoes sterile preparation. The patient then undergoes a liposuction procedure utilizing the Time-Machine™ device, fat processing unit (syringe) and 2.5-3 mm cannula. Bacitracin ointment and a band aid are secured over the wound along with a compressive bandage.

The SVF (ADSCs) are prepared in a closed system according to the following protocol:

a. TimeMachine® harvest of fat into 60 cc TP-101 syringe (single use sterile fat processing syringe)
b. Centrifuge at 2800 rpm for 3 min.
c. Remove free fatty acids and debris (local/blood) via TP-109 closed system
d. Transfer 25 cc of condensed fat to TP-102 syringe (SVF processing syringe)
e. Add pre-warmed (38° C.) 25 cc of Roche T-MAX® Time Machine Accelerator (GMP grade collagenase) containing 12.5 Wunsch units.
f. Incubate at 38° C. for 30-45 minutes.
g. Centrifuge at 200 g for 4 minutes
h. Remove supernatant fluid except for bottom 3-10 cc.
i. Add 50 cc DSLR as a washing solution to remove collagenase residue and centrifuge at 200 g for 4 minutes.
j. Repeat 2 more times for a total of 3 washings.
k. Remove all supernatant fluid leaving 3-10 cc of pellet collection—this is the Stromal Vascular Fraction.
l. Transfer SVF to labeled 20 cc syringe through 100-micron filters.
m. SVF sample collected and identified for number of cells, viability and to confirm no clumping or debris.
n. Aliquots of each cell suspension will be set aside for endotoxin testing and sterility staining. SVF will only be released for injection after confirmation of endotoxin assay results of level of EU less than or equal to 5 EU/kg/hr and negative gram stain results.
o. Cells will be resuspended in 20 ml of Isolyte. Cell suspensions will be drawn into a syringe through an 18-gauge needle for injection. Up to 100 million viable cells will be used for injection.
p. The syringe will then be placed in a sealed specimen bag labeled with the patient's name and medical record number for transport to the procedure room for injection.

Example 3: Administration of Adipose SVF with Smallpox Vaccine

Deployment methods:

a. Intravenous: the non-expanded, autologous stromal vascular fraction (SVF) extracted from up to 500 ml of lipoaspirate and purified by collagenase digestion and a series of washing steps and containing up to 100 million cells incubated with vaccinia virus will be delivered by intravenous injection in a volume of 20 mL.
b. Intra-tumoral: The non-expanded, autologous stromal vascular fraction (SVF) extracted from up to 500 ml of lipoaspirate and purified by collagenase digestion and a series of washing steps and containing cells incubated with vaccinia virus will be delivered by intratumoral injection. The injection volume and number of injected cells will vary and will depend on tumor type and tumor size and location.

Example 4: Oncolysis of Human Tumor Cell Lines After Infection with Lister and ACAM2000 Virus Strains In Vitro and Comparison of Solid Tumor Regression in A549 and PC3 Tumor-bearing Nude Mice Colonized with ACAM2000 or Lister Vaccinia Virus Strains In Vivo and Clinical Studies In Vitro To study comparatively the anti-tumoral activity of the smallpox vaccine ACAM2000, a panel of human cancer cell lines were infected with ACAM2000 and Lister virus strains at MOI of 0.01.

The breast cancer cells MDA-MB-231, lung adenocarcinoma cells A549 and NCI-H1299, prostate cancer cells PC3 and cervical cancer cells SiHa were seeded on 96-well plates 24 hours prior infection. The following day, cells were almost confluent and were infected with 50 µl of DMEM supplemented with 2% fetal bovine serum (FBS) containing appropriate amount of vaccinia virus (MOI of 0.01). Control cells were left untreated. After 1 hour of incubation the media were replaced with DMEM supplemented with 10% FBS. After 96 hours, tumor cell death was analyzed by MTT assay.

Cell death was measured 96 hours after infection with ACAM2000 or Lister Vaccinia virus (MOI of 0.01). Viability was measured by the colorimetric MTT assay. Optical density was measured at 570 nm. n=3. (A) Results are represented as percentage (%) of cell death normalized to untreated cells. (B) Table shows the comparison of ACAM2000 and Lister killing efficacy (+=1-25%, ++=26-50%, +++=51-75%, ++++=76-100%).

Figure 1B:
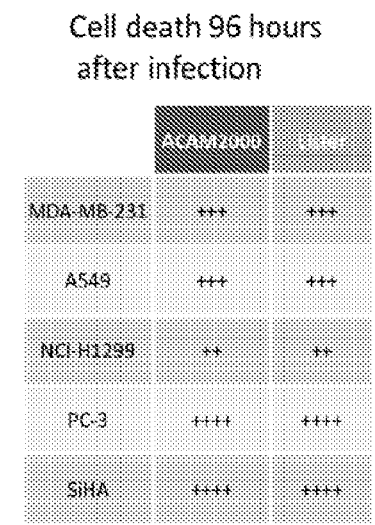

As shown in FIGS. 1A and 1B, ACAM2000 virus strain killed all human cancer cell lines efficiently with the exception of NCI-H1299 at comparable outcome than Lister virus strain (FIGS. 1A and 1B). Similar data was obtained with Copenhagen, MVA and other selected vaccinia virus strains.

In Vivo

To further study comparatively the anti-tumoral activity of the smallpox vaccines ACAM2000 and Lister, A549 and PC-3 tumor cells were injected subcutaneously in nude mice. Once tumor reached a volume of 350 mm3, animals were treated with a retroorbital injection containing the virus inoculum (5×106 PFU) (n=5). Control tumor-bearing mice were injected with Saline buffer. Comparable tumor growth inhibition occurred with both vaccinia virus samples 20 days after injection in A549 tumor bearing mice, and 14 days after virus injection in PC-3 tumor bearing mice. (Data not shown).

Clinical

Twenty-five patients with advanced metastatic solid tumors and hematologic malignancies have been treated with autologous stem cells/vaccinia virus combination in the StemImmune's recent trial. None of the 25 patients in this trial experienced any side effects resulting from the stem cell/vaccinia virus administration. Specifically, no fever, chills, or any other virus-related side effects were reported, in contrast to such side effects observed 6-12 hours after the administration of naked virus without stem cells in previous clinical trials. Importantly, all patients in the current trial experienced tumor location-specific "burning sensation" approximately 1 to 3 weeks after the stem cell/oncolytic virus administration, demonstrating effective delivery of the virus to the tumor sites and successful infection of the targeted tumors. Tumor size reduction and complete tumor eradication has been observed in some of the patients.

Serial blood samples were obtained from the treated patients before treatment (baseline sample), as well as at day 1, week 1, month 1, month 3, and month 6 after the treatment. Analysis of these samples revealed effective induction of cytokine release approximately 1 week after the treatment. Importantly, flow cytometry analysis confirmed the induction of activated T cells and memory T cells within one month of the treatment.

In summary, these results confirmed the i) significant safety of this treatment without any treatment-related side effects; ii) documented efficacy with tumor size reduction and even tumor eradication in some patients; and iii) effective induction of cytokine release and significant cellular response following this treatment.

Example 5: Clinical Trial of Adipose SVF with Smallpox Vaccine Study Design

The study evaluates the safety of deployment of adipose-derived SVF combined with ACAM2000 (SVF/ACAM2000) in patients with advanced solid tumors, based upon patient evaluation of subjective and objective findings. The antitumor effects of the adipose-derived SVF/ACAM200 administration also are evaluated, along with the presence of vaccinia virus within malignant tumors after SVF/ACAM200 injection by examination of resected/biopsied tumor specimen when applicable. In addition, the anti-vaccinia and antitumor immune responses following administration of SVF/ACAM2000 also are assessed.

All deployment techniques (intravenous and intra-tumoral) will be categorized regardless of condition in order to obtain information about specific deployment techniques. The study will follow each patient to determine if there were any adverse events following treatment with SVF/ACAM2000.

Inclusion Criteria

Patients (≥18 years) with histologically proven, primary or recurrent, advanced (staging defined by the American Joint Committee on Cancer (AJCC; 7th Edition) as stage III or IV, and/or aggressive (defined as published disease-specific survival rates less than 20% at 5 years following best currently available therapies) solid organ cancers.

Patients will provide written consent to allow a core needle biopsy samples of tumor tissue (primary or metastatic) to be obtained during baseline for analysis of mutations associated with his/her malignancy, for analysis of tumor cell sensitivity to vaccinia virus and for correlation studies. If available, patients may elect to provide a formalin fixed paraffin embedded tissue block (from his/her primary or metastatic tumor) obtained within 45 days prior to written consent for the clinical trial granting release of the paraffin block.

Criteria Include:
1. Ability to understand and the willingness to sign a written informed consent.
2. Histologically proven diagnosis of advanced (AJCC, 7th addition: stage III or IV) or aggressive (published disease-specific survival rates less than 20% at 5 years following best currently available therapies) solid organ cancer.

This includes but is not limited to:
   Metastatic melanoma;
   Esophageal and gastric adenocarcinoma (Stage III/IV);
   Cholangiocarcinoma (any stage);
   Pancreatic adenocarcinoma (any stage);
   Gallbladder cancer (any stage);
   High-grade mucinous appendix cancer (any stage);
   High-grade gastrointestinal neuroendocrine cancer (any stage);
   Mesothelioma (any stage);
   High-grade soft tissue sarcoma (any stage).
   Prostate cancer
   Renal cell carcinoma
   Lung small cell carcinoma
   Lung non-small cell carcinoma
   Head and neck Squamous cell carcinoma
   Colorectal cancer
   Ovarian carcinoma
   Hepatocellular Carcinoma
   Glioblastoma
3. Have NO continuing acute toxic effects of any prior therapy, including but not limited to biological therapy, radiotherapy, chemotherapy, or surgical procedures, i.e., all such effects must have resolved to Common Terminology Criteria for Adverse Events (CTCAE, Version 4.0) Grade≤1. Any other surgery (except biopsies) must have occurred at least 28 days prior to study enrollment.
4. ECOG performance Status of 0 to 2.

5. Have a life expectancy of at least 3 months.
6. Adequate organ and marrow function as defined below:
   Absolute neutrophil count (ANC)≥1.5×10$^9$;
   Platelets≥100×10$^9$ (without platelet transfusion);
   Hemoglobin≥9.0 g/dL (with or without red blood cell (RBC) transfusion);
   Serum creatinine≤1.5×upper limit of normal (ULN);
   Bilirubin≤1.5×ULN;
   ALT and AST at ≤2.5×ULN (in case of liver metastasis AST/ALT at ≤5.0×ULN;
   LDH≤1.5×ULN.
7. Women of child-bearing potential and men with partners of child-bearing potential must agree to use adequate contraception (hormonal or barrier method of birth control; abstinence) prior to study entry, for the duration of study participation, and for 90 days following completion of therapy. Should a woman become pregnant or suspect she is pregnant while participating in this study, she should inform her treating physician immediately.

A woman of child-bearing potential is any female (regardless of sexual orientation, having undergone a tubal ligation, or remaining celibate by choice) who meets the following criteria:
   Has not undergone a hysterectomy or bilateral oophorectomy; or
   Has not been naturally postmenopausal for at least 12 consecutive months (i.e., has had menses at any time in the preceding 12 consecutive months)
8. Women of child-bearing potential has negative pregnancy test prior to initiating study drug dosing
9. Be willing and able to comply with scheduled visits, the treatment plan, imaging and laboratory tests.

Exclusion Criteria
1. Current or anticipated use of other investigational agents or marketed anticancer agent while on study.
2. Patients who have received chemotherapy or radiotherapy within 4 weeks prior to entering the study or has not recovered from adverse events due to agents administered more than 4 weeks earlier.
3. Patients who are less than 4 weeks from surgery (except biopsies) or have insufficient recovery from surgical-related trauma or wound healing.
4. Have known immune system disorders (including acquired immunodeficiency syndrome (AIDS), HIV infection or hepatitis B or C). Eligible patients must have a negative HIV test result within 4 weeks prior to study initiation.
5. Patients who are receiving additional immunosuppressive therapy or any steroids (except concurrent corticosteroid usage if no more than 20 mg per day, prednisolone equivalent is applied).
6. Have received prior gene therapy or therapy with cytolytic virus of any type.
7. Have clinically significant cardiac disease (New York Heart Association Class III or IV) including pre-existing arrhythmia, uncontrolled angina pectoris, and myocardial infarction one year prior to study entry, or Grade 2 or higher compromised left ventricular ejection fraction.
8. Pulse oximetry oxygen saturation <90% at rest.
9. Have dementia or altered mental status that would prohibit informed consent.
10. Severe or uncontrolled medical disorder that would, in the investigator's opinion, impair ability to receive study treatment (i.e., uncontrolled diabetes, chronic renal disease, chronic pulmonary disease or active, fever, systemic and/or uncontrolled infections, psychiatric illness/social situations that would limit compliance with study requirements).
11. Be receiving concurrent antiviral agent active against vaccinia virus (e.g., cidofovir, vaccinia immunoglobulin, imatinib, ST-246) during the course of study.
12. Have known allergy to ovalbumin or other egg products.
13. Have clinically significant dermatological disorders (e.g., eczema, psoriasis, or any unhealed skin wounds or ulcers) as assessed by the Principal Investigator during screening and during the study.
14. Have a history of allergy to iodinated contrast media.
15. Patients with known brain metastases should be excluded from this clinical trial because of their poor prognosis and because they often develop progressive neurologic dysfunction that would confound the evaluation of neurologic and other adverse events.
16. Pregnant or nursing. There is a potential for congenital abnormalities and for this regimen to harm nursing infants.
17. Patients that are not accepted to the study because their condition does not seem to be one that can be improved with SVF/ACAM2000 as determined by one or more of our physician team.

Interventions, Administration, and Duration
Interventions will be as follows:
a) Patient will receive local anesthesia consisting of lidocaine 0.5% with epinephrine 1:400,000 with HCO3 8.4% titrated to pH of 7.4 (generally 5 cc of HCO3 in total volume of 60 cc).
b) Patient undergoes sterile prep.
c) Patient undergoes liposuction procedure utilizing the Time-Machine™ device, fat processing unit (syringe) and 2.5-3 mm cannula.
d) Bacitracin ointment and a Band-Aid are secured over the wound along with a compressive bandage.
e) The SVF (ADSCs) are prepared in a closed system according to the established protocol (see Page 5)

Deployment methods:
a. Intravenous: the non-expanded, autologous stromal vascular fraction (SVF) extracted from up to 500 ml of lipoaspirate and purified by collagenase digestion and a series of washing steps and containing up to 100 million cells incubated with vaccinia virus will be delivered by intravenous injection in a volume of 20 mL.
b. Intra-tumoral: the SVF incubated with vaccinia virus will be delivered by intratumoral injection at the Desert Medical Imaging in Palm Desert, CA The injection volume and number of injected cells will vary and will depend on tumor type and tumor size and location.

Dosing will be dependent upon individual yields. Should we find particular correlations with specific cell counts, then attempts may be made to optimize such counts for future patients. This, however, is not critical to the basic nature of this study and shouldn't affect its outcome.

Permitted Concomitant Therapy
Medications required to treat adverse events and manage cancer symptoms, concurrent stable disease (e.g., controlled hypertension), and supportive care agents such as erythropoietin or blood transfusion, and pain medications are allowed. The patient needs to notify the investigational site about any new medications he/she takes after the start of the study. All medications (other than study drug) and significant non-drug therapies (including physical therapy and blood transfusions) administered after the patient starts treatment with study drug must be recorded in the patient's medical record.

Below is a list of permitted supportive therapy/procedures:
Antiemetics;
Antidiarrheals;
Analgesics (e.g., non-steroidal anti-inflammatory drugs (NSAIDs) or oral or trans-dermal narcotic analgesics;
Antibiotics;
Nutritional and fluid supplementation;
Myeloid growth factors (except routine use of G-CSF and GM-CSF);
Bisphosphonates;
Blood transfusions and the use of erythropoietin are permitted at the discretion of the treating physician;
Prophylactic anticoagulant therapy (low dose) and full anticoagulation are allowed.
Prohibited Concomitant Therapy Other investigational therapies must not be used while the patient is on the study. Anti-cancer therapy (e.g., chemotherapy, biologic or radiation therapy, surgery) other than the study treatments must not be given to patients while the patient is on the study medication. If such agents are required for a patient, then the patient must be discontinued from the treatment portion of the study.

The list of non-permitted supportive therapy is listed below:
Surgery (other than the allowed surgical resection of primary tumor);
Other investigational treatment;
Other anti-cancer treatments;
Systemic immunosuppressants (except concurrent corticosteroid usage, if no more than 20 mg per day, prednisolone equivalent is applied);
Immunotherapy;
Routine prophylactic use of growth factor (G-CSF or GM-CSF).
Toxicities and Dosing Delays/Dose Modifications Any patient who receives treatment on this protocol will be evaluable for toxicity. Each patient will be assessed for the development of toxicity according to the NCI Common Toxicity Criteria for Adverse Events (CTCAE), version 4.03. A toxicity-related treatment delay of more than 2 weeks is defined as a DLT requiring withdrawal from study treatment.

Safety/Tolerability

Analyses will be performed for all patients having received at least one dose of study drug. The study will use the CTCAE version 4.03 (http://ctep.cancer.gov/reporting/ctc.html) for reporting of adverse events (Appendix B).

Antitumor Effect—Solid Tumors

Patients' disease status will be following by cross-sectional imaging.

Tumor Response Evaluation (From Stanford I.T. trial)

Tumor response rates will be calculated based on the Immune-related Response Criteria (irRC) (Wolchok et al., Guidelines for the evaluation of immune therapy activity in solid tumors: immune-related response criteria, *Clin. Cancer Res.* 2009, 15:7412-7420) in solid tumors, and secondarily with post-hoc assessment of response by Choi Criteria for gastrointestinal stromal tumors (GIST). See Choi et al., Correlation of computed tomography and positron emission tomography in patients with metastatic gastrointestinal stromal tumor treated at a single institution with imatinib mesylate: proposal of new computed tomography response criteria, *J. Clin. Oncol.* 2007, 25:1753-1759. Relevant tumor imaging studies will be obtained at baseline line, during treatment and follow-up at months 1, 3, and then every 3 months for 12 months, and then yearly.

As immune therapies may increase tumor burden (1) either due to continued tumor growth until immune response develops, or transient immune-cell infiltrate with or without edema, or (2) cause new lesions to appear (i.e., difficulty in differentiating new lesions from baseline, nonmeasurable lesions due to T-cell infiltration into established, radiographically undetectable tumor deposits), treatment should continue as tumors may begin to shrink after follow-up at a subsequent time point to confirm PD. Patients with stable performance status and laboratory values which have not significantly deteriorated, or who have moderate tumor growth on physical exam or radiographic imaging, should have repeat confirmation scans before true disease progression is defined and treatment is withdrawn. Continued treatment should be weighed against potential toxicity from continued treatment.

The primary analysis of activity is based on immune-related response criteria. Best Overall Response Rate (BORR), which is the number of patients with a BOR of CR or PR, divided by the number of treated patients. Disease control rate (DCR) is the number of patients with CR, PR or SD divided by the number of treated patients.

Overall survival (OS) is defined as the time from randomization until death from any cause.

Disease-free survival (DFS) is the time from randomization until recurrence of tumor or death from any cause.

Time-to-recurrence is defined as the time from duration from start of study treatment to the first occurrence of a recurrence event. A recurrence event is defined as clinical, radiographic, or pathologic evidence of new or persistent local, regional, or distant disease.

What is claimed is:

1. A composition, comprising:
(a) a smallpox vaccine; and (b) a stem cell, wherein the stem cell is selected from among adult stem cells, embryonic stem cells, fetal stem cells, mesenchymal stem cells, neural stem cells, totipotent stem cells, pluripotent stem cells, multipotent stem cells, oligopotent stem cells, unipotent stem cells, adipose stromal cells, endothelial stem cells, induced pluripotent stem cells, bone marrow stem cells, cord blood stem cells, adult peripheral blood stem cells, myoblast stem cells, small juvenile stem cells, skin fibroblast stem cells, and combinations thereof.

2. The composition of claim 1, wherein the stem cell is a neural stem cell.

3. The composition of claim 1, wherein the stem cell is a modified stem cell.

4. The composition of claim 3, wherein the modified stem cell is transformed with a virus or with plasmid DNA.

5. The composition of claim 1 that comprises a pharmaceutically acceptable carrier.

6. A composition, comprising:
adipose stromal cells; and
a poxvirus.

7. The composition of claim 6, wherein the poxvirus is a vaccinia virus.

8. The composition of claim 7, wherein the vaccinia virus and the adipose stromal cells were cultured together in vitro.

9. The composition of claim 7, wherein the vaccinia virus is a smallpox vaccine.

10. The composition of claim 7, wherein the vaccinia virus comprises heterologous DNA.

11. The composition of claim 9, wherein the smallpox vaccine is selected from among Dryvax, ACAM1000, ACAM2000, Lister, EM63, LIVP, Tian Tan, Copenhagen, Western Reserve, Modified Vaccinia Ankara (MVA), New York City Board of Health, Dairen, Ikeda, LC16M8, Tashkent, Wyeth, IHD-J, IHD-W, Brighton, Dairen I, and Connaught strains.

12. The composition of claim 9, wherein the smallpox vaccine is Dryvax, ACAM2000, or ACAM1000.

13. The composition of claim 6, wherein the adipose stromal cells are provided in an adipose-derived stromal vascular fraction (SVF).

14. The composition of claim 6, wherein the poxvirus and the adipose stromal cells were cultured together in vitro.

15. The composition of claim 14, wherein:
   the adipose stromal cells are provided in an adipose-derived stromal vascular fraction (SVF); and
   the SVF and the poxvirus were cultured together for 2 to 4 hours.

16. A pharmaceutical composition, comprising, in a pharmaceutically acceptable vehicle:
   adipose stromal cells; and
   a vaccinia virus.

17. The composition of claim 8, wherein the adipose stromal cells and the vaccinia virus were incubated together for 2-4 hours.

18. The composition of claim 17, wherein:
   the vaccinia virus is a smallpox vaccine; and
   the smallpox vaccine is selected from among ACAM1000, ACAM2000, Lister, LIVP, Modified Vaccinia Ankara (MVA), New York City Board of Health, IHD-J, IHD-W, Brighton, Dairen I, and Connaught strains.

19. The composition of claim 18, wherein the smallpox vaccine is ACAM1000 or ACAM2000.

* * * * *